US008362089B2

(12) United States Patent
Hashimoto

(10) Patent No.: US 8,362,089 B2
(45) Date of Patent: Jan. 29, 2013

(54) AQUEOUS COMPOSITION FOR COSMETICS AND COSMETIC INCLUDING THE SAME

(75) Inventor: Tomohiro Hashimoto, Osaka (JP)

(73) Assignee: Akzo Nobel N.V., Arnhem (NL)

( * ) Notice: Subject to any disclaimer, the term of this patent is extended or adjusted under 35 U.S.C. 154(b) by 642 days.

(21) Appl. No.: 12/021,077

(22) Filed: Jan. 28, 2008

(65) Prior Publication Data

US 2008/0131469 A1 Jun. 5, 2008

Related U.S. Application Data

(62) Division of application No. 10/827,666, filed on Apr. 19, 2004, now abandoned.

(30) Foreign Application Priority Data

May 14, 2003 (JP) ................................. 2003-135707

(51) Int. Cl.
*A61K 47/00* (2006.01)

(52) U.S. Cl. .......................... 514/778; 514/845; 514/846

(58) Field of Classification Search .................. 514/778, 514/845, 846
See application file for complete search history.

(56) References Cited

U.S. PATENT DOCUMENTS

| | | | |
|---|---|---|---|
| 3,137,592 A | 6/1964 | Protzman et al. | |
| 4,280,851 A | 7/1981 | Pitchon et al. | |
| 4,600,472 A | 7/1986 | Pitchon et al. | |
| 4,610,760 A | 9/1986 | Kirkpatrick et al. | |
| 4,616,074 A | 10/1986 | Ruffner | |
| 5,149,799 A | 9/1992 | Rubens | |
| 6,248,338 B1 | 6/2001 | Muller et al. | |
| 6,974,582 B2 * | 12/2005 | Yamato ........................ | 424/401 |
| 7,012,048 B2 | 3/2006 | Drovetskaya et al. | |
| 7,175,834 B2 | 2/2007 | Aust et al. | |
| 2003/0108505 A1 | 6/2003 | Cao et al. | |
| 2003/0147827 A1 | 8/2003 | DeCoster et al. | |
| 2004/0105833 A1 | 6/2004 | Fack et al. | |
| 2004/0105873 A1 | 6/2004 | Gupta | |
| 2005/0112157 A1 | 5/2005 | Ruppert et al. | |
| 2005/0158369 A1 | 7/2005 | Dorschner et al. | |

FOREIGN PATENT DOCUMENTS

| | | |
|---|---|---|
| JP | 62-81410 | 4/1987 |
| JP | 10-306123 | 11/1998 |
| JP | 11236310 A | 8/1999 |
| JP | 2000053552 A | 2/2000 |
| JP | 2000-234085 A | 8/2000 |
| JP | 2000-514435 A | 10/2000 |
| JP | 2003073237 A | 3/2003 |
| JP | 2003160427 A | 6/2003 |
| JP | 2004244633 A | 9/2004 |
| JP | 2004323425 A | 11/2004 |
| JP | 2005523308 A | 8/2005 |
| JP | 2005530718 A | 10/2005 |
| WO | WO 0154663 | 8/2001 |
| WO | WO 02078654 A1 | 10/2002 |
| WO | WO 03000212 | 1/2003 |

OTHER PUBLICATIONS

Questel QPAT English Abstract of JP10306123.
Questel QPAT English Abstract of JP2000234085.
International Cosmetic Ingredient Dictionary, 6th Edition, vol. 1, p. 20, 1995.

* cited by examiner

*Primary Examiner* — Renee Claytor
(74) *Attorney, Agent, or Firm* — Norris McLaughlin & Marcus, P.A.

(57) ABSTRACT

The invention provides an aqueous composition that can alleviate at least one of the problems that conventional aqueous compositions for cosmetics have (e.g., insufficient temporal stability, insufficient viscosity increase, being incapable of being used in a variety of pH ranges and being incapable of providing sufficient thixotropy). The aqueous composition for cosmetics includes: (A) at least one selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18 and a cross-linked product of an acyl modified starch with a carbon number of 2 to 18; and (B) a water-soluble polymer material. When the water-soluble polymer material (B) is an association type poly(meth)acrylate polymer, a nonionic or cationic cellulose polymer, a poly(meth)acrylic acid polymer or xanthan gum, the aqueous composition exhibits excellent viscosity increase ratio and temporal stability.

14 Claims, No Drawings

AQUEOUS COMPOSITION FOR COSMETICS AND COSMETIC INCLUDING THE SAME

CROSS-REFERENCE TO RELATED APPLICATIONS

The present application is a divisional application of U.S. application Ser. No. 10/827,666, filed 19 Apr. 2004, which is a continuation of Japanese Application No. 2003-135707, filed 14 May 2003.

BACKGROUND OF THE INVENTION

1. Field of the Invention

The present invention relates to aqueous compositions that can be used for cosmetics and to cosmetics containing the same.

2. Description of the Prior Art

Conventionally, a variety of polymer materials have been added to cosmetics for the purpose of increasing or modifying the viscosity of cosmetics and improving the feeling upon application of cosmetics. However, the addition of polymer materials leads to formation of films after drying and thus may cause the problem of a feeling of stiffness, so that it is desired to decrease the used amount of polymer materials.

As viscosity increasing agents capable of alleviating the above-described problems, viscosity increasing agents using semi-synthetic polymers such as cellulose polymers have been reported. These viscosity-increasing agents, however, do not provide a sufficient viscosity increase ratio, and the use of them may result in other problems of insufficient temporal stability and insufficient thixotropy.

On the other hand, it has been reported that the viscosity can be increased by combining a specific quaternary amine polymer (polyquaternium 6, which is classified as a cationic synthetic polyvinyl polymer) and a specific cross-linked starch product. This combination, however, yields an insufficient viscosity increase of about four times and can only be used in a specific pH range (see, e.g., JP2000-514435A (pp. 48-51)).

The present invention was achieved in order to solve the above-described problems, and it is an object of the present invention to provide an aqueous composition that can alleviate, or preferably substantially solve at least one of the problems of the conventional aqueous compositions for cosmetics, i.e., insufficient temporal stability, insufficient viscosity increase, being incapable of being used in a variety of pH ranges and being incapable of providing sufficient thixotropy. More preferably, the aqueous composition of the invention can alleviate all of the above-described problems, and most preferably, it can substantially solve all of the above-described problems. Furthermore, it is an object of the present invention to provide an aqueous composition with superior overall performance that can appropriately adjust the above-described properties.

SUMMARY OF THE INVENTION

As described below in detail, the inventor found as the result of extensive studies on aqueous compositions for cosmetics that an aqueous composition including a specific cross-linked starch product and a water-soluble polymer material can improve at least one of the problems of insufficient temporal stability, insufficient viscosity increase, being incapable of being used for a variety of pH ranges and being incapable of providing sufficient thixotropy, and thus achieved the present invention.

According to one aspect of the present invention, a novel aqueous composition is provided, which is an aqueous composition to be mixed in a cosmetic, including:

(A) at least one selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18 and a cross-linked product of an acyl modified starch with a carbon number of 2 to 18; and (B) a water-soluble polymer material.

In one mode of the present invention, the water-soluble polymer material (B) includes a poly(meth)acrylate polymer. The poly(meth)acrylate polymer is preferably an association type polymer, and the association type polymer may be either an anionic polymer or a cationic polymer.

In another mode of the present invention, the water-soluble polymer material (B) includes a nonionic cellulose polymer. The nonionic cellulose polymer is preferably hydroxyalkyl cellulose, and more preferably, hydroxyethyl cellulose.

In yet another mode of the present invention, the water-soluble polymer material (B) includes a cationic cellulose polymer. The cationic cellulose polymer is preferably O-[2-hydroxy-3-(trimethylammonio)propyl]hydroxyethyl cellulose chloride.

In a preferred mode of the present invention, the water-soluble polymer material (B) includes a poly(meth)acrylic acid polymer.

In another preferred mode of the present invention, the water-soluble polymer material (B) includes xanthan gum. Preferably, the xanthan gum is heat-treated at 60° C. or higher.

In a further preferred mode of the present invention, an aqueous composition is provided, in which the weight ratio of (A)/(B) is 30/1 to 0.5/1.

In another preferred mode of the present invention, an aqueous composition is proved, in which (A) constitutes 0.5 to 5.5 wt % of the whole of a cosmetic obtained by mixing the aqueous composition.

Preferably, an aqueous composition according to the present invention has a pH of 3 to 11, and is favorably used for cosmetics.

Accordingly, in another aspect of the present invention, a cosmetic including the above-described aqueous composition is provided.

In a preferred aspect of the present invention, a method for producing a cosmetic is provided, in which the above-described aqueous composition is mixed in such a manner that (A) constitutes 0.5 to 5.5 wt % of the whole of a cosmetic obtained by mixing the aqueous composition and the weight ratio of (A)/(B) is 30/1 to 0.5/1.

Further, a method for increasing the viscosity of a cosmetic is also provided, in which the above-described aqueous composition is mixed in such a manner that (A) constitutes 0.5 to 5.5 wt % of the whole of a cosmetic obtained by mixing the aqueous composition and the weight ratio of (A)/(B) is 30/1 to 0.5/1.

DESCRIPTION OF THE PREFERRED EMBODIMENTS

An aqueous composition according to the present invention is characterized by including: (A) at least one selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18 and a cross-linked product of an acyl modified starch with a carbon number of 2 to 18 (hereinafter, also referred to as "(A) cross-linked starch product"); and (B) a water-soluble polymer material.

In this specification, "aqueous" composition refers to compositions in which a cross-linked starch product and a water-soluble polymer material that are contained in the composition and other components that may be contained in the aqueous composition are present in an aqueous medium, and includes compositions in which these resins and the like are dissolved and/or dispersed in an aqueous medium.

It should be noted that throughout the specification, "part(s) by weight" and "wt %" are based on the portion other than the aqueous medium, unless otherwise described.

In this specification, "aqueous medium" refers to any kind of water, which includes, for example, distilled water and ion-exchange water. The "aqueous medium" may also include water-soluble or water-dispersible organic solvents, monomers, oligomers and the like, as long as the properties of the aqueous composition of the present invention and its use as a cosmetic described below are not adversely affected.

In the present invention, "(A) at least one selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18 and a cross-linked product of an acyl modified starch with a carbon number of 2 to 18 (or (A) cross-linked starch product)" refers to cross-linked starch products in which specific modified starches, that is, two types of modified starches, a hydroxyalkyl modified starch with a carbon number of 2 to 5 and an acyl modified starch with a carbon number of 2 to 18, are cross-linked between the same types or between different types (see JP2000-514435A).

Further, these cross-linked products may be used alone or in combination.

"Hydroxyalkyl modified starch with a carbon number of 2 to 5" refers to starches in which a hydroxyl group is bonded with the starch backbone via an alkyl group having a carbon number of C2 to C5, and which provide a suitable balance between hydrophilicity and lipophilicity. The position of the hydroxyl group in the alkyl group is not of decisive importance, and may be any given position. The substitution degree by the hydroxyalkylation is preferably 0.08 to 0.3. "Substitution degree" refers to an average number of hydroxyl groups of a starch molecule per anhydroglucol-unit. The hydroxyalkylation of a natural starch is achieved by reacting a natural starch with alkene oxide having only an appropriate number of carbon atoms of the natural starch. A hydroxyethylated starch and/or a hydroxypropylated starch that are obtained by reacting a starch with ethylene oxide or propylene oxide are particularly preferable. In addition, these may have a plurality of hydroxyl groups per alkyl group.

"Acyl modified starch with a carbon number of 2 to 18" refers to starches that are acylated by an acyl group with a carbon number of 2 to 18, which provide a suitable balance between hydrophilicity and lipophilicity. In general, the acylation is performed by reacting a starch with an acid anhydride represented by the general formula $(R-CO)_2O$, where R is an alkyl group such as a methyl group or an ethyl group.

The cross-linking of these modified starches is achieved with suitable cross-linking agents, that is, bifunctional compounds. Examples of preferred cross-linking methods include phosphorylation. In this case, the starches are reacted with phosphoryl chloride, phosphorus pentoxide and/or sodium trimetaphosphate. The two starches are cross-liked by an anion P—O radical. The anionic properties of the cross-linked site promote the function of the above-described modified starches to stabilize emulsion.

Further examples of preferred cross-linking methods include methods using alkanedicarboxylic acid or alkenedicarboxylic acid with a carbon number of C4 to C18. It is preferable to use alkanedicarboxylic acid with a carbon number of C4 to C8, particularly, adipic acid. Alkanedicarboxylic acid or alkenedicarboxylic acid with a carbon number of C4 to C18 provides a bonding between the two starches via an ester bound. The starches may be either linear or branched. A cross-linked product that is cross-linked by such dicarboxylic acid can be obtained by, for example, reacting the starch with a mixed anhydride of dicarboxylic acid and acetic acid. In the case of a dry starch, a cross-linking agent is generally used in an amount less than 0.1 wt %, and, normally, less than 0.6 wt %.

As the cross-linked starch products, hydroxypropyl distarch phosphate and acetylated distarch adipate are particularly preferable.

The starting starches used for obtaining the above-described specific starches may be any vegetable starches. Examples of such starting starches include corn, potato, wheat, rice, tapioca, sweet potato and sago. These starting starches preferably have an amylopectin content of at least 70 wt %, more preferably, at least 85 wt %, and most preferably, at least 90 wt %.

The above-described specific cross-linked starch product (A) is preferably gelatinized, and more preferably, completely gelatinized. As for the gelatinization, the starching starches may be previously gelatinized, or the cross-linked products may be gelatinized. Preferably, the specific cross-linked starch product (A) to be used is eventually gelatinized.

Examples of the commonly used methods for producing such starches include drum drying and extrusion spray drying.

Drum drying involves simultaneously performing the cooking and drying of highly viscous, semi-solid starch paste on a heating drum. Then, the resulting dried film is removed from the drum with a metal blade, followed by crushing. This step can be performed until the solid content is extremely large.

Extrusion drying can be used for simultaneously performing the cooking and drying of the starch (see U.S. Pat. No. 3,137,592). This method employs physical treatment of a starch/water mixture at high temperatures under high pressure, thus gelatinizing the starch. The starch discharged from the nozzle swells as a result of sudden evaporation of water.

By using a gelatinized cross-linked starch product (A), an aqueous composition according to the present invention can be produced at a temperature lower than the external temperature and a temperature used for producing known starch-containing compositions.

Preferably, a gelatinized cross-linked starch product (A) is produced by spray drying. Use of other methods, such as drum drying, tends to form a starch crust with low solubility, which may result in undissolved particles in an aqueous composition of the present invention.

Preferably, the major portion of the cross-linked starch product (A) consists of unbroken starch granules. A dispersion of a gelatinized starch derivative whose major portion has an unbroken granule structure has more homogeneous and smooth texture than a dispersion of a starch having no such a granule structure, which is obtained by, for example, drying a starch solution. In the case of a gelatinized starch having an intact granule structure, its appearance or external shape is maintained, although its original internal structure, i.e., hydrogen bond, is destroyed.

With regard to a method for producing a particularly preferable cross-linked product of gelatinized starches using spray drying, reference can be made to U.S. Pat. No. 4,280,851. As for an apparatus suitable for this method, reference can be made to U.S. Pat. No. 4,600,472. In this method, a granular starch or granular cross-linked starch product in an atomized state is cooked or gelatinized. The starch or cross-linked starch product to be cooked is atomized during it passes through an atomization inlet and enters into a nozzle device in such a manner that it becomes a relatively finely divided spray. Further, a heating medium is injected through an aperture in the nozzle device into the spray so as to heat the starch to a temperature required for gelatinization. An enclosed chamber surrounds the atomization and heating medium injection apertures, and defines a vent aperture positioned to enable the heated spray of the starch to exit the chamber. This apparatus is such that the elapsed time between passage of the spray of the starch through the chamber, i.e., from the atomization aperture and through the vent aperture, defines the gelatinization time of the starch. The resulting spray-dried starch, i.e., cross-linked starch product contains uniformly gelatinized starch particles in the form of indented sphere, a majority of which are whole and unbroken and swell after hydration. A nozzle that can be used to produce such a starch is described in U.S. Pat. No. 4,610,760.

For producing a preferable gelatinized starch or gelatinized cross-linked starch product, the method described in U.S. Pat. No. 5,149,799 may also be used. In this method, the starch is uniformly atomized and cooked in the presence of an aqueous medium by means of a single atomization step. The atomization step is performed in an apparatus including an internal mix two-fluid spray drying nozzle, and this apparatus is also connected to a device for drying the cooked, atomized starch.

A spray-dried, gelatinized preferable starch or cross-linked starch product can also be produced by a continuous, coupled jet-cooking and spray-drying process. A starch suspension is gelatinized at 138° C. to 160° C. in a jet cooker with direct steam injection. The streams of starch suspension and steam are mixed in a cooking or boiling chamber. The outlet of the latter is connected to a pneumatic spray nozzle or a high pressure nozzle, which is located in a conventional spray dryer. The jet-cooked starch is directed at elevated temperature and pressure into the spray nozzle and can be atomized with cold air, hot air, or preferably, steam. After atomizing, the hot, jet-cooked starch solution is handled in the same way as conventional spray dried starches. The drying process is adequately fast to prevent retrogradation of the starch particles during the cooling and drying of the spray. The spray-dried starch is amorphous material (i.e., it is substantially non-crystalline) which is easily soluble in water or colloidally dispersible.

An aqueous composition according to the present invention can be provided in any form, including, for example, solution, emulsion, suspension, gel or foam, and it can also be provided as a dry powdery composition. However, it is reconstituted to an aqueous composition in an aqueous medium upon use.

In addition, the cross-linked starch product (A) can also be used together with other starches such as natural starches and modified starches.

In the present invention, "water-soluble polymer material (B)" refers to water-soluble polymer materials that can be used for cosmetics, and there is no particular limitation. These can be used alone or in combination. Examples of the water-soluble polymer material (B) include natural polymers, semi-synthetic polymers and synthetic polymers.

Examples of "natural polymers" include plant- or animal-derived polysaccharides and proteins, and, in some cases, natural polymers that are subjected to fermentation treatment by microorganisms or heat treatment. These natural polymers can be classified into natural plant polymers, natural animal polymers, natural microorganism polymers and the like.

Examples of "natural plant polymers" include gum arabic, tragacanth gum, galactan, guar gum, carob gum, karaya gum, carrageenan, pectin, agar, quince seed (marmelo), algae colloid (algae extract), starches (derived from nice, corn, potato, wheat and the like) and glycyrrhizin.

Examples of "natural animal polymers" include collagen, casein, albumin and gelatin.

Examples of "natural microorganism polymers" include xanthan gum, dextran, succinoglucan and pullulan.

Natural microorganism polymers are preferable, and xanthan gum is particularly preferable. Heat-treated "natural microorganism polymers" are particularly preferable, and examples include heat-treated dehydroxanthan gum. The heat-treating temperature for xanthan gum is preferably at least 60° C., more preferably 80 to 200° C., and most preferably, 105 to 150° C.

"Semi-synthetic polymers" refer to, for example, semi-synthetic polymers that are obtained by modifying the above-described natural polymers, such as plant- or animal-derived polysaccharides and proteins, by means of chemical reaction, and there is no particular limitation. Examples include semi-synthetic starch polymers, semi-synthetic cellulose polymers, semi-synthetic alginic acid polymers and semi-synthetic microorganism polymers.

Examples of "semi-synthetic starch polymers" include solubilized starches, carboxymethyl starches, methylhydroxypropyl starches, modified potato starches and PEG-120 methylglucose oleate.

"Semi-synthetic cellulose polymers" can be classified into nonionic, anionic and cationic semi-synthetic cellulose polymers.

Examples of "nonionic semi-synthetic cellulose polymers" include: alkyl celluloses such as methylcellulose, methylethylcellulose, ethylcellulose and microcrystalline cellulose; and hydroxyalkyl celluloses such as hydroxyethyl cellulose, hydroxybutyl methylcellulose, hydroxypropyl cellulose, hydroxypropyl methylcellulose, hydroxyethyl methylcellulose, hydroxypropyl methylcellulose stearoxy ether, carboxymethylhydroxyethyl cellulose, alkylhydroxyethylcellulose and nonoxynyl hydroxyethylcellulose.

Examples of "anionic semi-synthetic cellulose polymers" include sodium cellulose sulfate, sodium carboxymethylcellulose (CMC) and their salts.

Examples of "cationic semi-synthetic cellulose polymers" include low nitrogen hydroxyethylcellulose dimethyldiallylammonium chloride (polyquaternium-4), O-[2-hydroxy-3-(trimethylammonio)propyl]hydroxyethylcellulose chloride (polyquaternium-10) and O-[2-hydroxy-3-(lauryldimethylammonio)propyl]hydroxyethylcellulose chloride (polyquaternium-24).

Examples of "semi-synthetic alginic acid polymers" include sodium alginate and propylene glycol alginate.

Examples of chemically modified "semi-synthetic microorganism polymers" include polymer compounds that are obtained by chemically modifying xanthan gum, dehydroxanthan gum, dextran, succinoglucan, pullulan and the like.

Nonionic semi-synthetic cellulose polymers and cationic semi-synthetic cellulose polymers are preferable, and hydroxyethylcellulose and O-[2-hydroxy-3-(trimethylammonio)propyl]hydroxyethylcellulose chloride are particularly preferable.

"Synthetic polymers" refer to any polymers that are synthetically produced by chemical reaction, and there is no particular limitation. Examples include poly(meth)acrylic acid polymers, poly(meth)acrylate polymers, polyvinyl polymers, polyurethane polymers and polyether polymers.

Examples of "poly(meth)acrylic acid polymers" include polyacrylic acid, polymethacrylic acid and their salts.

"Poly(meth)acrylate polymers" can be classified into "association type" and "non-association type" poly(meth)acrylate polymers.

"Association type poly(meth)acrylate polymers" refer to polymers that are generally called association type poly(meth)acrylate polymers, and there is no particular limitation. Examples of such polymers include chain polymers that may also have branches, whose molecular structures have a hydrophilic portion and a hydrophobic portion. Such polymers are disclosed in, for example, JP62-081410A, JP10-306123A and JP2000-234085A, the disclosures of which are herein incorporated by reference.

These association type poly(meth)acrylate polymers can be further classified into anionic and cationic association type poly(meth)acrylate polymers.

Examples of anionic association type poly(meth)acrylate polymers include: acrylates/alkyl PEG itaconate copolymers such as acrylates/steareth-20 itaconate copolymer, acrylates/ceteth-20 itaconate copolymer and acrylates/palmeth-25 itaconate copolymer; acrylates/alkyl PEG methacrylate copolymers such as acrylates/beheneth-25 methacrylate copolymer, acrylates/laureth-25 methacrylate copolymer, acrylates/ceteth-20 methacrylate copolymer and acrylates/steareth-20 methacrylate copolymer; and acrylates/alkyl PEG acrylate copolymers such as acrylates/palmeth-25 acrylate copolymer and acrylates/steareth-50 acrylate copolymer.

"Non-association type poly(meth)acrylate polymers" refer to poly(meth)acrylate polymers other than the above-described "association type poly(meth)acrylate polymers", and can be classified into anionic, cationic and amphoteric non-association type poly(meth)acrylate polymers.

Examples of "anionic non-association type poly(meth)acrylate polymers" include acrylates/C10-30 alkyl acrylate crosspolymer, acrylates/C10-30 alkyl acrylate polymer, acrylates/acetoacetoxyethyl methacrylate copolymer, acrylates/stearyl methacrylate copolymer, acrylates/vinyl isodecanoate crosspolymer, acrylates copolymer and acrylates/diacetoneacrylamide copolymer.

Examples of "cationic non-association type poly(meth)acrylate polymers" include vinylpyrrolidone/dimethylaminoethyl methacrylate/acrylate/PPG diacrylate copolymer, acrylic acid/methyl acrylate/methacryloyloxyethyl phosphorylcholine chloride/butyl methacrylate (polyquaternium-51).

Examples of "amphoteric non-association type poly(meth)acrylate polymers" include (octylacrylamide/hydroxypropyl acrylate/butylaminoethyl methacrylate) copolymer and methacryloyl alkyl betaine/acrylates copolymer.

"Polyvinyl polymers" can be classified into nonionic, cationic and amphoteric polyvinyl polymers.

Examples of "nonionic polyvinyl polymers" include polyacrylamide, polyvinyl alcohol, polyvinyl methyl ether, polyvinyl formamide and polyvinyl acetamide.

Examples of "cationic polyvinyl polymers" include dimethyldiallylammonium chloride/acrylamide (polyquaternium-7), diethyl sulfates of vinylpyrrolidone/N,N-dimethylaminoethyl methacrylate copolymer (polyquaternium-11), methyl sulfates of acrylamide/☐-methacryloxyethyl trimethylammonium copolymer (polyquaterternium-5), ammonium salts of methylvinyl imidazolinium chloride/vinylpyrrolidone copolymer (polyquaternium-16), vinylpyrrolidone/dimethylaminopropylamide methacrylate (polyquaternium-28), vinylpyrrolidone/imidazolinium ammonium (polyquaternium-44), vinylcaprolactam/vinylpyrrolidone/methylvinyl imidazolinium methylsulfate (polyquaternium-46), N-vinylpyrrolidone/N,N-dimethylaminoethyl methacrylate and N,N-dimethylaminoethyl methacrylate diethylsulfate.

Examples of "amphoteric polyvinyl polymers" include acrylamide/acrylic acid/dimethyldiallylammonium chloride (polyquaternium-39), dimethyldiallylammonium chloride/acrylic acid (polyquaternium-22) and dimethyldiallylammonium chloride/acrylic acid/acrylamide copolymer.

"Polyurethane polymers" can be classified into association type and non-association type polyurethane polymers.

Examples of "association type polyurethane polymers" include steareth-100/PEG-136/HDI copolymer.

Examples of "non-association type polyurethane polymers" include anionic polyether polyurethane, cationic polyether polyurethane, nonionic polyether polyurethane, amphoteric polyether polyurethane, anionic polyester polyurethane, cationic polyester polyurethane, nonionic polyester polyurethane and amphoteric polyester polyurethane.

Examples of "polyether polymers" include polyethylene glycol, polypropylene glycol and polyethylene glycol/polypropylene glycol.

Poly(meth)acrylic acid polymers and poly(meth)acrylate polymers are preferable, and association type poly(meth)acrylate polymers are particularly preferable.

Preferably, an aqueous composition according to the present invention generally includes 0.5 to 5.5 wt %, more preferably, 0.5 to 4.5 wt %, and most preferably, 0.5 to 3.5 wt % of the cross-linked starch product (A).

In an aqueous composition according to the present invention, the weight ratio of (A) cross-linked starch product/(B) water-soluble polymer material is preferably 30/1 to 0.5/1, more preferably, 30/1 to 1/1, and most preferably, 20/1 to 1/1.

When the water-soluble polymer material (B) is a poly(meth)acrylate polymer, the weight ratio of (A)/(B) is preferably 30/1 to 0.5/1, more preferably, 15/1 to 1/1, and most preferably, 10/1 to 1/1.

When the water-soluble polymer material (B) is a nonionic cellulose polymer, the weight ratio of (A)/(B) is preferably 30/1 to 0.5/1, more preferably, 15/1 to 1/1, and most preferably, 10/1 to 1/1.

When the water-soluble polymer material (B) is a cationic cellulose polymer, the weight ratio of (A)/(B) is preferably 30/1 to 0.5/1, more preferably, 15/1 to 1/1, and most preferably, 10/1 to 1/1.

When the water-soluble polymer material (B) is a poly(meth)acrylic acid polymer, the weight ratio of (A)/(B) is preferably 30/1 to 0.5/1, more preferably, 30/1 to 5/1, and most preferably, 20/1 to 5/1.

When the water-soluble polymer material (B) is xanthan gum, the weight ratio of (A)/(B) is preferably 30/1 to 0.5/1, more preferably, 20/1 to 1/1, and most preferably, 15/1 to 1/1.

The pH of an aqueous composition according to the present invention is preferably 3.0 to 11.0, more preferably, 3.5 to 10.0, and most preferably, 4.0 to 9.0.

Additionally, in the present invention, "pH" refers to values that are measured at 30° C. with a pH-meter (pH-meter F13 (trade name) manufactured by Horiba, Ltd.).

When the water-soluble polymer material (B) is a poly (meth)acrylate polymer, the pH of the aqueous composition is preferably 3.0 to 11.0, more preferably, 3.5 to 10.0, and most preferably, 4.0 to 9.0.

When the water-soluble polymer material (B) is a nonionic cellulose polymer, the pH of the aqueous composition is preferably 3.0 to 11.0, more preferably, 3.5 to 10.0, and most preferably, 4.0 to 9.0.

When the water-soluble polymer material (B) is a cationic cellulose polymer, the pH of the aqueous composition is preferably 3.0 to 11.0, more preferably, 3.5 to 10.0, and most preferably, 4.0 to 9.0.

When the water-soluble polymer material (B) is a poly (meth)acrylic acid polymer, the pH of the aqueous composition is preferably 6.0 to 11.0, more preferably, 7.0 to 10.0, and most preferably, 7.0 to 9.0.

When the water-soluble polymer material (B) is xanthan gum, the pH of the aqueous composition is preferably 3.0 to 10.0, more preferably, 3.5 to 9.5, and most preferably, 4.0 to 9.0.

An aqueous composition of the present invention is superior with regard to the temporal stability as evaluated by the method described in the example below. That is, when a viscosity measurement is carried out by the prescribed method, the difference between the initial viscosity and the viscosity after 3-month storage is less than ±10%, and particularly preferably, less than ±5%.

Furthermore, an aqueous composition of the present invention is superior with regard to the viscosity increase ratio as evaluated by the method described in the example below. That is, the viscosity increase ratio represented by the following Equation (I) is preferably at least 10, more preferably, at least 15, and most preferably, at least 20.

Viscosity increase ratio=viscosity of aqueous solution of mixture of ($A$) and ($B$)/[(viscosity of aqueous solution of ($A$)+viscosity of aqueous solution of ($B$))/2]    Equation (I)

In Equation (I), "viscosity of aqueous solution of mixture of (A) and (B)" means a viscosity of an aqueous composition including (A) and (B), and "(Viscosity of aqueous solution of (A)+viscosity of aqueous solution of (B))/2" means an arithmetic mean of a viscosity of an aqueous solution of (A) and a viscosity of an aqueous solution of (B).

An aqueous composition of the present invention is superior with regard to the thixotropy as evaluated by the method described in the example below. That is, when a viscosity measurement is carried out by a predetermined method described below, a thixotropy calculated according to the following Equation (II) is preferably as large as possible. More specifically, the thixotropy is preferably at least 1.5, more preferably, 2.0 to 100, and most preferably, 2.5 to 10.

Thixotropy=viscosity at 4 rpm/viscosity at 20 rpm    Equation (II)

In addition, the above-described aqueous composition according to the present invention may appropriately contain various additives, in order to improve a variety of properties. Such additives may be, for example, the below-described additives contained in cosmetics.

The above-described aqueous composition can be suitably used for cosmetics.

Accordingly, the present invention provides a cosmetic including the above-described aqueous composition.

Preferably, the above-described aqueous composition of the present invention is mixed in such a manner that (A) constitutes 0.5 to 5.5 wt %, more preferably 0.5 to 4.5 wt %, and most preferably, 0.5 to 3.5 wt % of the whole of a cosmetic obtained by mixing the aqueous composition (based on the whole of the cosmetic).

Further, in the aqueous composition according to the present invention, the weight ratio of (A) cross-linked starch product/(B) water-soluble polymer material is preferably 30/1 to 0.5/1, more preferably, 30/1 to 1/1, and most preferably, 20/1 to 1/1 in a cosmetic obtained by mixing the aqueous composition.

When the water-soluble polymer material (B) is a poly (meth)acrylate polymer, the weight ratio of (A)/(B) is preferably 30/1 to 0.5/1, more preferably, 15/1 to 1/1, and most preferably, 10/1 to 1/1.

When the water-soluble polymer material (B) is a nonionic cellulose polymer, the weight ratio of (A)/(B) is preferably 30/1 to 0.5/1, more preferably, 15/1 to 1/1, and most preferably, 10/1 to 1/1.

When the water-soluble polymer material (B) is a cationic cellulose polymer, the weight ratio of (A)/(B) is preferably 30/1 to 0.5/1, more preferably, 15/1 to 1/1, and most preferably, 10/1 to 1/1.

When the water-soluble polymer material (B) is a poly (meth)acrylic acid polymer, the weight ratio of (A)/(B) is preferably 30/1 to 0.5/1, more preferably, 30/1 to 5/1, and most preferably, 20/1 to 5/1.

When the water-soluble polymer material (B) is xanthan gum, the weight ratio of (A)/(B) is preferably 30/1 to 0.5/1, more preferably, 20/1 to 1/1, and most preferably, 15/1 to 1/1.

A cosmetic according to the present invention may, as necessary, appropriately contain various additives. Examples include water, lower alcohols such as ethanol, nonionic surfactants, anionic surfactants, cationic surfactants, amphoteric surfactants, amino acid-based surfactants, fatty acid soaps, oils and fats, waxes, hydrocarbon oils, ester oils, higher alcohols, polyhydric alcohols, silicons (or silicones), powders, ultraviolet absorbers, antiseptics, antibacterial agents, aroma chemicals, antioxidants, pH modifiers, chelating agents, refrigerants, antiinflammatory agents and skin care components (e.g., skin-lightening agents, cell activators, skin roughness inhibitors and blood circulation promoters).

"Anionic surfactants" refer to any anionic surfactants that are commonly used for cosmetics, and there is no particular limitation.

Examples of anionic surfactants include the following compounds:

polyoxyethylene alkyl ether sulfates such as sodium polyoxyethylene lauryl ether sulfate and ammonium polyoxyethylene lauryl ether sulfate;

alkyl sulfates such as sodium lauryl sulfate and ammonium lauryl sulfate;

sodium polyoxyethylene alkyl ether acetate such as sodium polyoxyethylene tridecyl ether acetate and sodium polyoxyethylene lauryl ether acetate;

alkyl sulfosuccinates such as dialkylsulfosuccinic acid, polyoxyalkylene alkyl sulfosuccinate and dioctyl sodium sulfosuccinate;

polyoxyethylene fatty acid amide ether sulfate, sodium cocoyl methyl taurate, N-acyl-L-aspartate, cocoyl ethyl ester sulfonate, sodium alkyl☐-alanine, acylmethyl taurine, alkyl ethane sodium sulfonate, sodium polyoxyethylene alkyl ether carboxylate, alkane sulfonate, olefin sulfonate and alkyl benzene sulfonate.

The anionic surfactants may be used alone or in combination.

"Nonionic surfactants" refer to any nonionic surfactants that are commonly used for cosmetics, and there is no particular limitation.

Examples of nonionic surfactants include the following compounds:
  polyoxyethylene alkyl ethers such as polyoxyethylene lauryl ether, polyoxyethylene cetyl ether, polyoxyethylene stearyl ether, polyoxyethylene oleyl ether and polyoxyethylene behenyl ether,
  polyoxyethylene polyoxypropylene alkyl ethers such as polyoxyethylene polyoxypropylene cetyl ether and polyoxyethylene polyoxypropylene decyltetradecyl ether;
  diethanolamides such as coconut oil fatty acid diethanolamide, lauric acid diethanolamide, myristic acid diethanolamide, palmitic acid diethanolamide, stearic acid diethanolamide, isostearic acid diethanolamide and oleic acid diethanolamide;
  monoethanolamides such as coconut oil fatty acid monoethanolamide, lauric acid monoethanolamide, myristic acid monoethanolamide, palmitic acid monoethanolamide, stearic acid monoethanolamide, isostearic acid monoethanolamide and oleic acid monoethanolamide;
  isopropanolamides such as coconut oil fatty acid isopropanolamide, lauric acid isopropanolamide, myristic acid isopropanolamide, palmitic acid isopropanolamide, stearic acid isopropanolamide, isostearic acid isopropanolamide and oleic acid isopropanolamide;
  polyoxyethylene monoethanolamides such as polyoxyethylene coconut oil fatty acid monoethanolamide, polyoxyethylene lauric acid monoethanolamide, polyoxyethylene myristic acid monoethanolamide, polyoxyethylene palmitic acid monoethanolamide, polyoxyethylene stearic acid monoethanolamide, polyoxyethylene isostearic acid monoethanolamide and polyoxyethylene oleic acid monoethanolamide;
  alkyl glucosides such as decyl glucoside and lauryl glucoside;
  alkyl dimethylamine oxides such as lauryl dimethylamine oxide and stearyl dimethylamine oxide;
  hydroxyl fatty acid alkyl maltitol ether, alkylated polysaccharides, saccharose fatty acid ester and fatty acid isopropanolamide.

The nonionic surfactants may be used alone or in combination.

"Cationic surfactants" refer to any cationic surfactants that are commonly used for cosmetics, and there is no particular limitation.

Examples of cationic surfactants include the following compounds:
  alkyl trimethyl ammonium chlorides such as lauryl trimethyl ammonium chloride, cetyl trimethyl ammonium chloride, stearyl trimethyl ammonium chloride and behenyl trimethyl ammonium chloride;
  alkyl dimethyl ammonium chlorides such as distearyl dimethyl ammonium chloride and dialkyl (C12 to 18) dimethyl ammonium chloride;
  lanolin derivatives of quaternary ammonium salts, behenyl dimethyl hydroxyethyl ammonium chloride and stearyl dimethyl benzyl ammonium chloride.

The cationic surfactants may be used alone or in combination.

"Amphoteric surfactants" refer to any amphoteric surfactants that are commonly used for cosmetics, and there is no particular limitation.

Examples of amphoteric surfactants include the following compounds:
  acetic acid betaines such as lauryldimethylaminoacetic acid betaine, trialkylaminoacetic acid betaine and stearyldimethylaminoacetic acid betaine;
  amidopropylbetaines such as lauric acid amidopropylbetaine, coconut oil fatty acid amidopropylbetaine, myristic acid amidopropylbetaine and cocoalkyl-N-carboxyethyl-N-hydroxyethyl imidazolinium betaine; and
  imidazolinium betaines such as alkyl-N-hydroxyethyl-N-carboxymethylimidazolinium betaine and 2-alkyl-N-carhoxymethyl-N-hydroxyethylimidazoliinum betaine.

The amphoteric surfactants may be used alone or in combination.

"Amino acid-based surfactants" refer to any amino acid-based surfactants that are commonly used for cosmetics, and there is no particular limitation.

Examples of amino acid-based surfactants include the following compounds:
  glutamates such as triethanolamine salts, sodium salts and potassium salts of N-coconut oil fatty acid acyl-L-glutamic acid, lauroyl-L-glutamic acid, myristoyl-L-glutamic acid, stearoyl-L-glutamic acid and the like;
  glycine salts such as triethanolamine salts, sodium salts and potassium salts of N-coconut oil fatty acid acyl glycine, lauroyl glycine, myristoyl glycine, stearoyl glycine and the like;
  alanine salts such as triethanolamine salts, sodium salts and potassium salts of N-coconut oil fatty acid acyl alanine, lauroyl alanine, myristoyl alanine, stearoyl alanine and the like;
  sarcosine salts such as triethanolamine salts, sodium salts and potassium salts of N-coconut oil fatty acid acyl sarcosine, lauroyl sarcosine, myristoyl sarcosine, stearoyl sarcosine and the like;
  N-coconut oil fatty acid acyl-L-arginine ethyl DL-pyrrolidone carboxylate, N-acyl taurate and N-acyl methyltaurine.

The amino acid-based surfactants may be used alone or in combination.

"Fatty acid soaps" refer to any fatty acid soaps that are commonly used for cosmetics, and there is no particular limitation. Examples of fatty acid soaps include alkali salts of C6-24 higher fatty acids. The fatty acids may be either saturated or unsaturated, and examples include capric acid, lauric acid, myristic acid, palmitic acid, stearic acid, isostearic acid, arachidic acid, behenic acid, oleic acid, isooleic acid, linoleic acid, linolenic acid and arachidonic acid. In addition, the alkalis for neutralizing the fatty acids may be any alkalis that are commonly used for producing soaps, and there is no particular limitation. Examples include caustic potash, caustic soda, triethanolamine, N-methyltaurine and ammonia.

The fatty acid soaps may be used alone or in combination.

"Oils and fats" may be any oils and fats that are commonly used for cosmetics, and there is no particular limitation. Examples of oils and fats include avocado oil, camellia oil, evening primrose oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, China wood oil, Japanese wood oil, jojoba oil, germ oil, triglycerol, glyceryl trioctanoate, glycerol triisopalmitate, cacao butter, coconut oil, hardened coconut oil, palm oil, palm kernel oil, Japan wax kernel oil, hardened oil, hardened castor oil and their polyoxyethylene adducts.

The fats and oils may be used alone or in combination.

"Waxes" refer to any waxes that are commonly used for cosmetics, and there is no particular limitation. Examples of waxes include spermaceti, beeswax, high acid number beeswax, shellac, mink wax, lanolin, lanolin acetate, liquid lanolin, carnauba wax, candelilla wax, rice bran wax, bran wax, Japan wax, cotton wax, bayberry wax, Chinese insect wax (Ibota wax), montan wax, kapok wax, jojoba wax, sugarcane wax, lanolin fatty acid isopropyl, hexyl laurate, reduced lanolin, hard lanolin, shellac wax, POE lanolin alcohol ether, POE lanolin alcohol acetate, POE cholesterol ether, lanolin fatty acid polyethylene glycol and POE hydrogenated lanolin alcohol ether.

The waxes may be used alone or in combination.

"Hydrocarbon oils" refer to any hydrocarbon oils that are commonly used for cosmetics, and there is no particular limitation.

Examples of hydrocarbon oils include oil components of paraffin, liquid paraffin, ozokerite, squalene, pristine, ceresin, vaseline and microcrystalline wax.

The hydrocarbon oils may be used alone or in combination.

"Ester oils" refer to any ester oils that are commonly used for cosmetics, and there is no particular limitation.

Examples of ester oils include the following compounds:
myristates such as isopropyl myristate, butyl myristate, myristyl myristate, isocetyl myristate, octyldodecyl myristate and 2-hexyldecyl myristate;
palmitates such as isopropyl palmitate, cetyl palmitate, isostearyl palmitate, 2-ethylhexyl palmitate, 2-hexyldecyl palmitate and 2-heptylundecyl palmitate;
stearates such as butyl stearate, isocetyl stearate, cholesteryl stearate, isocetyl isostearate, cholesteryl 12-hydroxystearate and N-alkylglycol isostearate;
laurates such as isopropyl laurate and hexyl laurate;
linoleates such as ethyl linoleate and isopropyl linoleate;
octanoates such as cetyl octanoate, hexyldecyl dimethyloctanoate, octyldodecyl dimethyloctanoate and cetyl isooctanoate;
oleates such as decyl oleate and oleic acid oil;
sorbitan fatty acid ester oils such as sorbitan monolaurate, sorbitan monopalmitate, sorbitan monostearate, sorbitan sesquistearate, sorbitan tristearate, sorbitan monooleate, sorbitan sesquioleate, sorbitan trioleate, sorbitan monoisostearate and sorbitan sesquiisostearate;
polyoxyethylene sorbitan fatty acid esters such as polyoxyethylene sorbitan monococoate, polyoxyethylene sorbitan monopalmitate, polyoxyethylene sorbitan monostearate, polyoxyethylene sorbitan monoisostearate, polyoxyethylene sorbitan tristearate and polyoxyethylene sorbitan monooleate;
polyoxyethylene sorbitol fatty acid esters such as polyoxyethylene sorbitol monolaurate, polyoxyethylene sorbitol hexastearate, polyoxyethylene sorbitol tetrastearate and polyoxyethylene sorbitol tetraoleate;
lactates such as cetyl lactate and myristyl lactate;
malates such as diisostearyl malate;
adipates such as diisobutyl adipate, di-2-heptylundecyl adipate and 2-hexyldecyl adipate;
sebacates such as di-2-ethylhexyl sebacate and diisopropyl sebacate;
succinates such as 2-ethylhexyl succinate;
citrates such as triethyl citrate, triisocetyl citrate, triisoarachyl citrate, triisooctyl citrate, acetyltriethyl citrate and acetyltributyl citrate;
polyhydric alcohol esters such as ethylene glycol di-2-ethylhexanoate, propylene glycol monocaprate, propylene glycol dicaprate, propylene glycol didecanoate, glyceryl tri-2-ethylhexanoate, glyceryl tri(caprylate/caprate), trimethylolpropane tri-2-ethylhexanoate, trimethylolpropane triisostearate, pentaerythritol tetra-2-ethylhexanoate, glyceryl trimyristate, decaglyceryl decastearate, decaglyceryl decaoleate, decaglyceryl decaisostearate, glyceryl di-2-heptylundecanoate, polyoxyethylene glyceryl monostearate, polyethylene glycol glyceryl monooleate, diglyceryl monostearate, diglyceryl monoisostearate, diglyceryl monooleate, tetraglyceryl monostearate, polyglyceryl monooleate, polyglyceryl tristearate, polyglyceryl pentastearate, polyglyceryl pentaoleate and neopentyl glycol dicaprate;
lanolin acetate, dipentaerythritol fatty acid ester, glyceride tri-2-heptylundecanoate, castor oil fatty acid methyl ester, acetoglyceride, N-lauroyl-L-glutamic acid-2-octyldodecyl ester and ethyl laurate.

The ester oils may be used alone or in combination.

"Higher alcohols" refer to any higher alcohols that are commonly used for cosmetics, and there is no particular limitation. Examples of higher alcohols include lauryl alcohol, cetyl alcohol, stearyl alcohol, cetostearyl alcohol, cetearyl alcohol, behenyl alcohol, myristyl alcohol, oleyl alcohol, batyl alcohol, capryl alcohol, 2-decyltetradecinol, lanolin alcohol, cholesterol, phytosterol, hexyl dodecanol, isostearyl alcohol and octyl dodecanol.

The higher alcohols may be used alone or in combination.

"Polyhydric alcohols" refer to any polyhydric alcohols that are commonly used for cosmetics, and there is no particular limitation. Examples of polyhydric alcohols include 1,2-propanediol, 1,3-propanediol, 1,2-butanediol, 1,3-butanediol, 1,4-butanediol, dipropylene glycol, glycerol, diglycerol, sorbitan, sorbitol and maltitol.

The polyhydric alcohols may be used alone or in combination.

"Silicons" refer to any silicons that are commonly used for cosmetics, and there is no particular limitation. Examples of silicons include amino modified silicons such as amodimethicone, polyether modified silicons such as dimethicone polyol, cyclic silicons such as cyclomethicone, dimethicones such as methyl polysiloxane and highly polymerized methyl polysiloxane, phenyl modified silicons such as methylphenyl polysiloxane, and alkyl modified silicons and alkoxy modified silicons.

The silicons may be used alone or in combination.

"Powders" refer to any powders that are commonly used for cosmetics, and there is no particular limitation. Powders can be used regardless of their shapes (e.g., spherical, needle-shaped and plate-shaped), particle sizes (e.g., fume form, and fine particle and pigment grades), particle structures (e.g., porous and nonporous) and the like.

Examples of "inorganic powders" include titanium oxide, zirconium oxide, zinc oxide, cerium oxide, magnesium oxide, barium sulfate, calcium sulfate, magnesium sulfate, calcium carbonate, magnesium carbonate, talcs, synthetic micas, micas, kaolin, sericite, muscovite, phlogopite, lepidolite, biotite, lithia mica, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, diabasic calcium phosphate, alumina, aluminum hydroxide, boron nitride and silica.

Examples of "organic powders" include polyamide powder, polyester powder, polyethylene powder, polypropylene powder, polystyrene powder, polyurethane powder, benzoguanamine powder, polymethylbenzoguanamine powder, tetrafluoroethylene powder, polymethyl methacrylate powder, celluloses, silk powder, nylon powder, Nylon 12, Nylon 6, styrene-acrylic acid copolymers, divinylbenzene-styrene copolymers, vinyl resins, urea resins, phenolic resins, fluororesins, silicon resins, acrylic resins, melamine resins, epoxy resins, polycarbonate resins, microcrystalline fiber powder, rice starch and lauroyl lysine.

The powders may be used alone or in combination.

"Ultraviolet absorbers" refer to any ultraviolet absorbers that are commonly used for cosmetics, and there is no particular limitation.

Examples of ultraviolet absorbers include the following compounds:

benzophenone derivatives such as 2-hydroxy-4-methoxybenzophenone, 2-hydroxy-4-methoxybenzophenone-5-sulfonic acid, 2-hydroxy-4-methoxybenzophenone-5-sodium sulfonate, dihydroxymethoxybenzophenone, dihydroxymethoxybenzophenone-sodium sulfonate, 2,4-dihydroxybenzophenone and tetrahydroxybenzophenone;

p-aminobenzoic acid derivatives such as p-aminobenzoic acid, ethyl p-aminobenzoate, glyceryl p-aminobenzoate, amyl p-dimethylaminobenzoate and octyl p-dimethylaminobenzoate;

methoxycinnamic acid derivatives such as ethyl p-methoxycinnamate, isopropyl p-methoxycinnamate, octyl p-methoxycinnamate, 2-ethoxyethyl p-methoxycinnamate, sodium p-methoxycinnamate, potassium p-methoxycinnamate and glyceryl mono-2-ethylhexanoate p-metoxy cinnamate;

salicylic acid derivatives such as octyl salicylate, phenyl salicylate, homomenthyl salicylate, dipropylene glycol salicylate, ethylene glycol salicylate, myristyl salicylate and methyl salicylate;

urocanic acid, ethyl urocanate, ethyl urocanate ester, 4-tert-butyl-4'-methoxybenzoylmethane, 2-(2'-hydroxy-5'-methylphenyl) benzotriazole, 2-phenyl-5-methylbenzoxazole, methyl anthranilate and 2-ethylhexyl dimethoxybenzylidene dioxoimidazolidine propionate.

The ultraviolet absorbers may be used alone or in combination.

"Moisturizing agents" refer to any moisturizing agents that are commonly used for cosmetics, and there is no particular limitation.

Examples of moisturizing agents include sorbitol, xylitol, propylene glycol, dipropylene glycol, 1,3-butylene glycol, glycerol, diglycerol, polyethylene glycol, hyaluronic acid, chondroitin sulfuric acid, pyrrolidone carboxylate and DL-pyrrolidone carboxylate.

The moisturizing agents may be used alone or in combination.

"Antiseptics" refer to any antiseptics that are commonly used for cosmetics, and there is no particular limitation.

Examples of antiseptics include p-oxybenzoic acid alkyl ester, benzoic acid, sodium benzoate, sorbic acid, potassium sorbate, phenoxyethanol, dehydroacetic acid and their salts.

The antiseptics may be used alone or in combination.

"Antibacterial agents" refer to any antibacterial agents that are commonly used for cosmetics, and there is no particular limitation.

Examples of antibacterial agents include benzoic acid, salicylic acid, carbolic acid, sorbic acid, p-oxybenzoic acid ester, parachlorometacresol, hexachlorophene, benzalkonium chloride, chlorhexidine chloride, trichlorocarbanilide, photosensitive agents and phenoxyethanol.

The antibacterial agents may be used alone or in combination.

"Antioxidants" refer to any antioxidants that are commonly used for cosmetics, and there is no particular limitation.

Examples of antioxidants include tocopherol, butylhydroxyanisole and dibutylhydroxytoluene.

The antioxidants may be used alone or in combination.

"pH modifiers" refer to any pH modifiers that are commonly used for cosmetics, and there is no particular limitation.

Examples of pH modifiers include lactic acid, citric acid, glycolic acid, succinic acid, tartaric acid, dl-malic acid, potassium carbonate, sodium hydrogen carbonate and ammonium hydrogen carbonate.

The pH modifiers may be used alone or in combination.

"Chelating agents" refer to any chelating agents that are commonly used for cosmetics, and there is no particular limitation.

Examples of chelating agents include alanine, sodium edetate, sodium polyphosphate, sodium metaphosphate and phosphoric acid.

The chelating agents may be used alone or in combination.

"Refrigerants" refer to any refrigerants that are commonly used for cosmetics, and there is no particular limitation.

Examples of refrigerants include L-menthol and camphor.

The refrigerants may be used alone or in combination.

"Antiinflammatory agents" refer to any antiinflammatory agents that are commonly used for cosmetics, and there is no particular limitation.

Examples of antiinflammatory agents include allantoin, glycyrrhetinic acid, tranexamic acid and azulene.

The antiinflammatory agents may be used alone or in combination.

A cosmetic of the present invention may be prepared in any forms that are commonly used for cosmetics, and there is no particular limitation. For example, a cosmetic according to the present invention can be used in a variety of forms, including solution, dispersion, cream, O/W or W/O emulsion, paste, gel, aerosol and multilayer separate liquid.

It should be noted that "cosmetics" refer to any cosmetics for which the above-described aqueous composition of the present invention can be used, and there is no particular limitation. Examples of such cosmetics include cleansing cosmetics, hair cosmetics, make-up cosmetics, skin care cosmetics and oral cosmetics.

Examples of "cleansing cosmetics" include shampoos, rinses, conditioners, hand soaps, body soaps, face washes and make-up cleansers.

Examples of "hair cosmetics" include hair foams, hair gels, nonaerosol pump sprays, hair creams, hair waxes, acidic hair dyes, hair colorants, perming agents and bleaching agents.

Examples of "make-up cosmetics" include manicures, mascaras, eyeliners, eye shadows, liquid foundations, lipsticks and cheek rouges.

Examples of "skin care cosmetics" include foundations, packs, sunscreens, skin lotions, milky lotions and skin creams.

Furthermore, the present invention provides a method for producing a cosmetic, preferably, a cosmetic with improved viscosity, in which the above-described aqueous composition is mixed such that (A) constitutes 0.5 to 5.5 wt % of the whole of a cosmetic obtained by mixing the aqueous composition and the weight ratio of (A)/(B) is 30/1 to 0.5/1. It is more preferable to mix the aqueous composition such that (A) constitutes 0.5 to 4.5 wt % and the weight ratio of (A)/(B) is 30/1 to 1/1, and it is most preferable to mix the aqueous composition such that (A) constitutes 0.5 to 3.5 wt % and the weight ratio of (A)/(B) is 20/1 to 1/1.

The present invention also provides a method for increasing the viscosity of a cosmetic in which method the above-described aqueous composition is mixed such that (A) constitutes 0.5 to 5.5 wt % of the whole of a cosmetic obtained by mixing the aqueous composition and the weight ratio of (A)/

(B) is 30/1 to 0.5/1. It is more preferable to mix the aqueous composition such that (A) constitutes 0.5 to 4.5 wt % and the weight ratio of (A)/(B) is 30/1 to 1/1, and it is most preferable to mix the aqueous composition such that (A) constitutes 0.5 to 3.5 wt % and the weight ratio of (A)/(B) is 20/1 to 1/1.

EXAMPLES

The components listed in the following Tables 1 to 4 were mixed in the ratios shown in Tables 1 to 4, and the mixture was stirred until it became homogeneous, thereby producing samples of Examples 1 to 15 and Comparative Examples 1 to 12. It should be noted that the numerical values described in the tables are the values of active ingredients (i.e., the portions other than an aqueous medium) and indicate wt %.

The properties of the obtained samples were measured as follows.

Viscosity

The viscosity was measured with a Brookfield viscometer at a temperature of 30° C. at a rotating speed of 10 rpm, using spindles Nos. 1 to 7. It should be noted that the unit of the viscosity shown in Tables 1 to 4 is Pa·s.

pH

The pH was measured with a pH meter (pH meter F13 (trade name) manufactured by Horiba, Ltd.) at 30° C.

Viscosity Increase Ratio

As the viscosity increase ratio obtained by mixing the cross-linked starch product (A) and the water-soluble polymer material (B), a value represented by the following Equation (I) was used.

Viscosity increase ratio=viscosity of aqueous solution of mixture of (A) and (B)/[(viscosity of aqueous solution of (A)+viscosity of aqueous solution of (B))/2]   Equation (I)

In Equation (I), "viscosity of aqueous solution of mixture of (A) and (B)" means a viscosity of an aqueous composition including (A) and (B). More specifically, it refers to the viscosity values of the samples of Examples 1 to 11 shown in Tables 1 to 2. "(viscosity of aqueous solution of (A)+viscosity of aqueous solution of (B))/2" means an arithmetic mean of a viscosity of an aqueous solution of (A) and a viscosity of an aqueous solution of (B). More specifically, "viscosity of aqueous solution of (A)" refers to the viscosity value of the sample of Comparative Example 12 shown in Table 4, and "viscosity of aqueous solution of (B)" refers to the viscosity values of the samples of Comparative Examples 1 to 11 shown in Tables 3 to 4.

Thixotropy

The thixotropy was evaluated by the ratio of the viscosity values obtained by measuring the viscosity at different rotating speeds. The viscosity was measured with a Brookfield viscometer at a temperature of 30° C. at rotating speeds of 20 rpm and 4 rpm, using spindles Nos. 1 to 7. The thixotropy was determined according to the following Equation (II).

Thixotropy=viscosity at 4 rpm/viscosity at 20 rpm   Equation (II)

It can be said that the closer the value to 1, the poorer the thixotropy is, and the greater the value, the better the thixotropy is.

Temporal Stability

The temporal stability was evaluated as follows.

After storing the solutions of the examples and the comparative examples for three months at room temperature, their viscosities were measured by a predetermined method. The temporal stability was evaluated based on the following evaluation criteria:

"A" means that the difference between the initial viscosity and the viscosity after 3-month storage was less than ±5%;

"B" means that the difference between the initial viscosity and the viscosity after 3-month storage was ±5% or more and less than ±10%;

"C" means that the difference between the initial viscosity and the viscosity after 3-month storage was ±10% or more and less than ±40%; and "D" means that the difference between the initial viscosity and the viscosity after 3-month storage was ±40% or more.

The components used for producing the samples of Examples 1 to 15 and Comparative Examples 1 to 12 are described in the following.

As the cross-linked starch product (A), (a1) hydroxypropyl starch phosphate (STRUCTURE XL (trade name) manufactured by National Starch and Chemical Company) was used.

As the water-soluble polymer material (B), the following (b1) to (b11) were used:

(b1) dehydroxanthan gum (AMAZE XT (trade name) manufactured by National Starch and Chemical Company), which is a heat-treated natural microorganism polymer;

(b2) hydroxyethyl cellulose (Natrosol 250 HHR (trade name) manufactured by Hercules Inc.), which is a nonionic semi-synthetic cellulose polymer;

(b3) hydroxypropyl methylcellulose (Metolose 65 SH-4000 (trade name) manufactured by Shin-Etsu Chemical Co. Ltd.), which is a nonionic semi-synthetic cellulose polymer;

(b4) carboxymethylcellulose (CELLOGEN (trade name) manufactured by DAI-ICHI KOGYO SEIYAKU CO. LTD.), which is an anionic semi-synthetic cellulose polymer;

(b5) polyquaternium-4 (CELQUAT L-200 (trade name) manufactured by National Starch and Chemical Company), which is a cationic semi-synthetic cellulose polymer;

(b6) polyquaternium-10 (CELQUAT SC-240C (trade name) manufactured by National Starch and Chemical Company), which is a cationic semi-synthetic cellulose polymer;

(b7) polyacrylic acid (Carbopol 940 (trade name) manufactured by BF Goodrich Co.), which is a poly(meth) acrylic acid synthetic polymer;

(b8) (acrylates/steareth-20 itaconate) copolymer (STRUCTURE 2001 (trade name) manufactured by National Starch and Chemical Company), which is an anionic association type synthetic poly(meth)acrylate polymer;

(b9) (acrylates/aminoacrylate/C10-30 Alkyl PEG-20 Itaconate) copolymer (STRUCTURE PLUS (trade name) manufactured by National Starch and Chemical Company), which is a cationic association type synthetic poly(meth)acrylate polymer;

(b10) (acrylic acid/alkyl acrylate (C10-30)) copolymer (Carbopol EDT 2020 (trade name) manufactured by BF Goodrich Co.), which is an anionic non-association type synthetic poly(meth)acrylate polymer; and (b11) polyquaternium-7 (Merquat 2200 (trade name) manufactured by ONDEO Nalco Company), which is a cationic synthetic polyvinyl polymer.

TABLE 1

| | Example | | | | | | | | |
|---|---|---|---|---|---|---|---|---|---|
| | 1 | 2 | 3 | 4 | 5 | 6 | 7 | 8 | 9 |
| (A)(a1) | 3.0 | 3.0 | 3.0 | 3.0 | 3.0 | 3.0 | 3.0 | 3.0 | 3.0 |
| (B)(b1) | 0.25 | — | — | — | — | — | — | — | — |
| (b2) | — | 1.0 | — | — | — | — | — | — | — |
| (b3) | — | — | 2.0 | — | — | — | — | — | — |
| (b4) | — | — | — | 2.0 | — | — | — | — | — |
| (b5) | — | — | — | — | 2.0 | — | — | — | — |
| (b6) | — | — | — | — | — | 2.0 | — | — | — |
| (b7) | — | — | — | — | — | — | 0.1 | — | — |
| (b8) | — | — | — | — | — | — | — | 0.5 | — |
| (b9) | — | — | — | — | — | — | — | — | 1.0 |
| (b10) | — | — | — | — | — | — | — | — | — |
| (b11) | — | — | — | — | — | — | — | — | — |
| Triethanolamine | — | — | — | — | — | — | Proper amount | Proper amount | — |
| Glycolic acid | — | — | — | — | — | — | — | — | Proper amount |
| Water | Remainder | Remainder | Remainder | Remainder | Remainder | Remainder | Remainder | Remainder | Remainder |
| Whole amount | 100 | 100 | 100 | 100 | 100 | 100 | 100 | 100 | 100 |
| Viscosity (Pa·s) | 20 | 20 | 25 | 8 | 4 | 10 | 20 | 900 | 100 |
| Viscosity increase ratio | 16.0 | 26.7 | 20.0 | 10.7 | 12.3 | 28.6 | 26.7 | 720 | 100 |
| pH | 5.5 | 6.7 | 6.7 | 6.5 | 6.7 | 5.7 | 8.5 | 8.2 | 5.5 |
| Thixotropy | 3.31 | 2.69 | 2.54 | 2.01 | 2.21 | 2.48 | 3.01 | 3.21 | 3.00 |
| Temporal stability | A | A | B | B | B | A | A | A | A |

TABLE 2

| | Example | | | | | |
|---|---|---|---|---|---|---|
| | 10 | 11 | 12 | 13 | 14 | 15 |
| (A)(a1) | 3.0 | 3.0 | 0.5 | 0.5 | 0.5 | 5.0 |
| (B)(b1) | — | — | — | — | — | — |
| (b2) | — | — | — | 1.0 | — | — |
| (b3) | — | — | — | — | — | — |
| (b4) | — | — | — | — | — | — |
| (b5) | — | — | — | — | — | — |
| (b6) | — | — | — | — | — | 1.0 |
| (b7) | — | — | — | — | — | — |
| (b8) | — | — | 0.5 | — | — | — |
| (b9) | — | — | — | — | 1.0 | — |
| (b10) | 1.0 | — | — | — | — | — |
| (b11) | — | 1.0 | — | — | — | — |
| Triethanolamine | Proper | — | — | — | — | — |
| Glycolic acid | — | — | — | — | — | — |
| Water | Remainder | Remainder | Remainder | Remainder | Remainder | Remainder |
| Whole amount | 100 | 100 | 100 | 100 | 100 | 100 |
| Viscosity (Pa·s) | 30 | 5.0 | 7.0 | 4.5 | 4.0 | 20 |
| Viscosity increase ratio | 24.0 | 12.5 | 10.0 | 12.5 | 10.0 | 39.7 |
| pH | 6.5 | 6.2 | 8.0 | 6.5 | 5.0 | 5.5 |
| Thixotropy | 3.07 | 2.39 | 3.19 | 2.21 | 2.81 | 2.71 |
| Temporal stability | B | B | B | B | B | B |

TABLE 3

| | Comparative Example | | | | | | | | |
|---|---|---|---|---|---|---|---|---|---|
| | 1 | 2 | 3 | 4 | 5 | 6 | 7 | 8 | 9 |
| (A)(a1) | — | — | — | — | — | — | — | — | — |
| (B)(b1) | 0.25 | — | — | — | — | — | — | — | — |
| (b2) | — | 1.0 | — | — | — | — | — | — | — |
| (b3) | — | — | 2.0 | — | — | — | — | — | — |
| (b4) | — | — | — | 2.0 | — | — | — | — | — |
| (b5) | — | — | — | — | 2.0 | — | — | — | — |
| (b6) | — | — | — | — | — | 2.0 | — | — | — |
| (b7) | — | — | — | — | — | — | 0.1 | — | — |
| (b8) | — | — | — | — | — | — | — | 0.5 | — |
| (b9) | — | — | — | — | — | — | — | — | 1.0 |
| (b10) | — | — | — | — | — | — | — | — | — |
| (b11) | — | — | — | — | — | — | — | — | — |
| Triethanol-amine | — | — | — | — | — | — | Proper amount | Proper amount | — |
| Glycolic acid | — | — | — | — | — | — | — | — | Proper amount |
| Water | Remainder | Remainder | Remainder | Remainder | Remainder | Remainder | Remainder | Remainder | Remainder |
| Whole amount | 100 | 100 | 100 | 100 | 100 | 100 | 100 | 100 | 100 |
| Viscosity (Pa·s) | 2.00 | 1.00 | 2.00 | 1.00 | 0.15 | 0.20 | 1.00 | 2.00 | 15.0 |
| pH | 5.4 | 6.7 | 6.8 | 6.4 | 6.7 | 6.8 | 8.2 | 8.3 | 5.3 |
| Thixotropy | 2.25 | 1.81 | 1.45 | 1.36 | 1.42 | 1.62 | 1.95 | 2.43 | 2.03 |
| Temporal stability | D | D | D | D | D | D | C | C | C |

TABLE 4

| | Comparative Example | | |
|---|---|---|---|
| | 10 | 11 | 12 |
| (A)(a1) | — | — | 3.0 |
| (B)(b1) | — | — | — |
| (b2) | — | — | — |
| (b3) | — | — | — |
| (b4) | — | — | — |
| (b5) | — | — | — |
| (b6) | — | — | — |
| (b7) | — | — | — |
| (b8) | — | — | — |
| (b9) | — | — | — |
| (b10) | 0.3 | — | — |
| (b11) | — | 2.0 | — |
| Triethanolamine | — | — | — |
| Glycolic acid | — | — | — |
| Water | Remainder | Remainder | Remainder |
| Whole amount | 100 | 100 | 100 |
| Viscosity (Pa·s) | 2.00 | 0.30 | 0.50 |
| pH | 8.1 | 6.2 | 6.1 |
| Thixotropy | 1.9 | 1.23 | 1.97 |
| Temporal stability | C | D | D |

As described above, the aqueous compositions including (A) and (B) according to the present invention have excellent dispersion stability, exhibit excellent viscosity increase ratio and are superior with regard to, for example, providing thixotropy. The aqueous compositions including an association type synthetic poly(meth)acrylate polymer as (B) exhibit a viscosity increase ratio of 100 times or more, and are particularly excellent.

The above-described aqueous compositions according to the present invention can be used for a variety of cosmetics. Examples of the cosmetics including these aqueous compositions are shown below.

As examples of the cleansing cosmetics, shampoos, rinses and body soaps were produced.

As for the shampoos, the ingredients listed in Table 5 were mixed at the ratios shown in Table 5, and the mixture was dissolved at 80° C., followed by stirring until it became homogeneous. Thereafter, the mixture was cooled to room temperature, thereby producing a shampoo.

TABLE 5

| Shampoo | Example | | | Comparative Example | | | |
|---|---|---|---|---|---|---|---|
| Composition | 21 | 22 | 23 | 21 | 22 | 23 | 24 |
| Sodium laureth sulfate | 10.0 | 10.0 | 10.0 | 10.0 | 10.0 | 10.0 | 10.0 |
| Cocamidopropyl betaine | 5.0 | 5.0 | 5.0 | 5.0 | 5.0 | 5.0 | 5.0 |
| Cocamido MEA | 2.0 | 2.0 | 2.0 | 2.0 | 2.0 | 2.0 | 2.0 |
| Lauramidopropyl betaine | 1.0 | 1.0 | 1.0 | 1.0 | 1.0 | 1.0 | 1.0 |
| Glycol distearate | 2.0 | 2.0 | 2.0 | 2.0 | 2.0 | 2.0 | 2.0 |
| Dimethicone | 1.0 | 1.0 | 1.0 | 1.0 | 1.0 | 1.0 | 1.0 |
| Dimethicone polyol | 1.0 | 1.0 | 1.0 | 1.0 | 1.0 | 1.0 | 1.0 |

TABLE 5-continued

| Shampoo | Example | | | Comparative Example | | | |
|---|---|---|---|---|---|---|---|
| Composition | 21 | 22 | 23 | 21 | 22 | 23 | 24 |
| Potassium cocoyl glutamate | 0.5 | 0.5 | 0.5 | 0.5 | 0.5 | 0.5 | 0.5 |
| Laureth-4 | 1.0 | 1.0 | 1.0 | 1.0 | 1.0 | 1.0 | 1.0 |
| Hydrolyzed collagen | 0.2 | 0.2 | 0.2 | 0.2 | 0.2 | 0.2 | 0.2 |
| Panthenol | 0.2 | 0.2 | 0.2 | 0.2 | 0.2 | 0.2 | 0.2 |
| Citric acid | 0.1 | 0.1 | 0.1 | 0.1 | 0.1 | 0.1 | 0.1 |
| Antiseptic | Proper amount | Proper amount | Proper amount | Proper amount | Proper amount | Proper amount | Proper amount |
| (a1) | 1.0 | 1.0 | 1.0 | — | — | — | 1.0 |
| (b1) | 0.5 | — | — | 0.5 | — | — | — |
| (b6) | — | 0.5 | — | — | 0.5 | — | — |
| (b8) | — | — | 0.5 | — | — | 0.5 | — |
| Water | Remainder | Remainder | Remainder | Remainder | Remainder | Remainder | Remainder |
| Total | 100 | 100 | 100 | 100 | 100 | 100 | 100 |

As for the rinses, the components from stearyl alcohol to glutamic acid listed in Table 6 were mixed at the ratios shown in Table 6, and the mixture was dissolved at 80° C., preparing an oil phase. Next, the components from stearyl trimethyl ammonium chloride to water were mixed at the ratios shown in Table 6, and the mixture was dissolved at 80° C., preparing a water phase. Then, the oil phase was charged into the water phase, and the mixture was emulsified with a homomixer, followed by stirring until it became homogeneous. Thereafter, the mixture was cooled to room temperature, thereby producing a rinse.

TABLE 6

| Rinse | Example | | | Comparative Example | | | |
|---|---|---|---|---|---|---|---|
| Composition | 25 | 26 | 27 | 25 | 26 | 27 | 28 |
| Stearyl alcohol | 5.0 | 5.0 | 5.0 | 5.0 | 5.0 | 5.0 | 5.0 |
| Behenyl alcohol | 5.0 | 5.0 | 5.0 | 5.0 | 5.0 | 5.0 | 5.0 |
| Dimethicone | 3.0 | 3.0 | 3.0 | 3.0 | 3.0 | 3.0 | 3.0 |
| Behentrimonium chloride | 1.0 | 1.0 | 1.0 | 1.0 | 1.0 | 1.0 | 1.0 |
| Amodimethicone | 1.0 | 1.0 | 1.0 | 1.0 | 1.0 | 1.0 | 1.0 |
| Octyl palmitate | 0.5 | 0.5 | 0.5 | 0.5 | 0.5 | 0.5 | 0.5 |
| Glutamic acid | 0.5 | 0.5 | 0.5 | 0.5 | 0.5 | 0.5 | 0.5 |
| Stearyltrimethyl-ammonium chloride | 1.0 | 1.0 | 1.0 | 1.0 | 1.0 | 1.0 | 1.0 |
| Glycerol | 3.0 | 3.0 | 3.0 | 3.0 | 3.0 | 3.0 | 3.0 |
| Propylene glycol | 1.5 | 1.5 | 1.5 | 1.5 | 1.5 | 1.5 | 1.5 |
| Laureth-4 | 0.5 | 0.5 | 0.5 | 0.5 | 0.5 | 0.5 | 0.5 |
| Antiseptic | Proper amount | Proper amount | Proper amount | Proper amount | Proper amount | Proper amount | Proper amount |
| (a1) | 1.0 | 1.0 | 1.0 | — | — | — | 1.0 |
| (b1) | 0.5 | — | — | 0.5 | — | — | — |
| (b2) | — | 0.5 | — | — | 0.5 | — | — |
| (b9) | — | — | 0.5 | — | — | 0.5 | — |
| Water | Remainder | Remainder | Remainder | Remainder | Remainder | Remainder | Remainder |
| Total | 100 | 100 | 100 | 100 | 100 | 100 | 100 |

As for the body soaps, the ingredients listed in Table 7 were mixed at the ratios shown in Table 7, and the mixture was dissolved at 80° C., followed by stirring until it became homogeneous. Thereafter, the mixture was cooled to room temperature, thereby producing a body soap.

TABLE 7

| Body soap | Example | | | Comparative Example | | | |
|---|---|---|---|---|---|---|---|
| Composition | 31 | 32 | 33 | 31 | 32 | 33 | 34 |
| Potassium laurate | 8.0 | 8.0 | 8.0 | 8.0 | 8.0 | 8.0 | 8.0 |
| Potassium palmitate | 3.0 | 3.0 | 3.0 | 3.0 | 3.0 | 3.0 | 3.0 |
| Potassium myristate | 5.0 | 5.0 | 5.0 | 5.0 | 5.0 | 5.0 | 5.0 |
| Potassium stearate | 3.0 | 3.0 | 3.0 | 3.0 | 3.0 | 3.0 | 3.0 |
| Propylene glycol | 5.0 | 5.0 | 5.0 | 5.0 | 5.0 | 5.0 | 5.0 |
| Glycol distearate | 1.0 | 1.0 | 1.0 | 1.0 | 1.0 | 1.0 | 1.0 |
| Sodium laureth sulfate | 0.5 | 0.5 | 0.5 | 0.5 | 0.5 | 0.5 | 0.5 |
| Cocamidopropyl betaine | 0.5 | 0.5 | 0.5 | 0.5 | 0.5 | 0.5 | 0.5 |
| Cocamido DEA | 1.0 | 1.0 | 1.0 | 1.0 | 1.0 | 1.0 | 1.0 |
| Antiseptic | Proper amount | Proper amount | Proper amount | Proper amount | Proper amount | Proper amount | Proper amount |
| (a1) | 1.0 | 1.0 | 1.0 | — | — | — | 1.0 |
| (b1) | 0.5 | — | — | 0.5 | — | — | — |
| (b3) | — | 0.5 | — | — | 0.5 | — | — |
| (b8) | — | — | 0.5 | — | — | 0.5 | — |
| Water | Remainder | Remainder | Remainder | Remainder | Remainder | Remainder | Remainder |
| Total | 100 | 100 | 100 | 100 | 100 | 100 | 100 |

As examples of the hair cosmetics, hair foams, hair gels, hair creams, hair waxes and hair colorants were produced.

As for the hair foams, the components from laureth-12 to water (i.e., the components other than propellant) listed in Table 8 were mixed at the ratios shown in Table 8, and the mixture was stirred until it became homogeneous. To this mixture, propellant was added at the ratio shown in Table 8, thereby producing a hair foam.

TABLE 8

| Hair foam | Example | | | | Comparative Example | | | | |
|---|---|---|---|---|---|---|---|---|---|
| Composition | 41 | 42 | 43 | 44 | 41 | 42 | 43 | 44 | 45 |
| Laureth-12 | 0.5 | 0.5 | 0.5 | 0.5 | 0.5 | 0.5 | 0.5 | 0.5 | 0.5 |
| Ceteth-20 | 0.5 | 0.5 | 0.5 | 0.5 | 0.5 | 0.5 | 0.5 | 0.5 | 0.5 |
| 1,3-butylene glycol | 1.0 | 1.0 | 1.0 | 1.0 | 1.0 | 1.0 | 1.0 | 1.0 | 1.0 |
| Dimethicone | 0.5 | 0.5 | 0.5 | 0.5 | 0.5 | 0.5 | 0.5 | 0.5 | 0.5 |
| Dimethicone polyol | 0.5 | 0.5 | 0.5 | 0.5 | 0.5 | 0.5 | 0.5 | 0.5 | 0.5 |
| Stearyltrimethyl-ammonium chloride | 0.1 | 0.1 | 0.1 | 0.1 | 0.1 | 0.1 | 0.1 | 0.1 | 0.1 |
| Sorbitan stearate | 0.1 | 0.1 | 0.1 | 0.1 | 0.1 | 0.1 | 0.1 | 0.1 | 0.1 |
| Ethanol | 10.0 | 10.0 | 10.0 | 10.0 | 10.0 | 10.0 | 10.0 | 10.0 | 10.0 |
| (a1) | 1.0 | 1.0 | 1.0 | 1.0 | — | — | — | — | 1.0 |
| (b1) | 1.0 | — | — | — | 1.0 | — | — | — | — |
| (b12) | — | 1.0 | — | — | — | 1.0 | — | — | — |
| (b13) | — | — | 3.0 | — | — | — | 3.0 | — | — |
| (b14) | — | — | — | 3.0 | — | — | — | 3.0 | — |
| Antiseptic | Proper amount | Proper amount | Proper amount | Proper amount | Proper amount | Proper amount | Proper amount | Proper amount | Proper amount |
| Water | Remainder | Remainder | Remainder | Remainder | Remainder | Remainder | Remainder | Remainder | Remainder |
| Propellant (LPG) | 8.0 | 8.0 | 8.0 | 8.0 | 8.0 | 8.0 | 8.0 | 8.0 | 8.0 |
| Total | 100 | 100 | 100 | 100 | 100 | 100 | 100 | 100 | 100 |

As for the hair gels, the components from propylene glycol to (b16) (i.e., the components other than the components from triethanolamine to an antiseptic) listed in Table 9 were mixed at the ratio shown in Table 9, and the mixture was stirred until it became homogeneous. To this mixture, the components from triethanolamine to an antiseptic were added at the ratios shown in Table 9, thereby producing a hair gel.

As for the hair waxes, the components from vaseline to triethanolamine (i.e., the components other than the components from glycerol to (b17)) listed in Tables 11 and 12 were mixed at the ratios shown in Tables 11 and 12, and the mixture

TABLE 9

| Hair gel | Example | | | Comparative Example | | | |
|---|---|---|---|---|---|---|---|
| Composition | 51 | 52 | 53 | 51 | 52 | 53 | 54 |
| Propylene glycol | 0.5 | 0.5 | 0.5 | 0.5 | 0.5 | 0.5 | 0.5 |
| Dimethicone Polyol | 0.2 | 0.2 | 0.2 | 0.2 | 0.2 | 0.2 | 0.2 |
| Polyoxyethylene hardened castor oil | 0.1 | 0.1 | 0.1 | 0.1 | 0.1 | 0.1 | 0.1 |
| Water | Remainder | Remainder | Remainder | Remainder | Remainder | Remainder | Remainder |
| (a1) | 1.0 | 1.0 | 1.0 | — | — | — | 1.0 |
| (b1) | 1.0 | — | — | 1.0 | — | — | — |
| (b12) | — | 0.5 | — | — | 0.5 | — | — |
| (b15) | — | — | 3.0 | — | — | 3.0 | — |
| Triethanolamine | Proper amount | Proper amount | Proper amount | Proper amount | Proper amount | Proper amount | Proper amount |
| Ethanol | 10.0 | 10.0 | 10.0 | 10.0 | 10.0 | 10.0 | 10.0 |
| Antiseptic | Proper amount | Proper amount | Proper amount | Proper amount | Proper amount | Proper amount | Proper amount |
| Total | 100 | 100 | 100 | 100 | 100 | 100 | 100 |

As for the hair creams, the components from liquid paraffin to an antiseptic (i.e., the components other than the components from (a1) to water) listed in Table 10 were mixed at the ratios shown in Table 10, and the mixture was dissolved at 80° C., preparing an oil phase. Next, the components from (a1) to water were mixed at the ratios shown in Table 10, and the mixture was dissolved at 80° C., preparing a water phase. The oil phase was charged into the water phase, and the mixture was emulsified with a homomixer, followed by stirring until it became homogeneous. Thereafter, the mixture was cooled to room temperature, thereby producing a hair cream.

was dissolved at 80° C., preparing an oil phase. Next, the components from glycerol to (b17) were mixed at the ratios shown in Tables 11 and 12, and the mixture was dissolved at 80° C., preparing a water phase. The oil phase was charged into the water phase, and the mixture was emulsified with a homomixer, followed by stirring until it became homogeneous. Thereafter, the mixture was cooled to room temperature, thereby producing a hair wax.

TABLE 10

| Hair cream | Example | | | | Comparative Example | | | | |
|---|---|---|---|---|---|---|---|---|---|
| Composition | 61 | 62 | 63 | 64 | 61 | 62 | 63 | 64 | 65 |
| Liquid paraffin | 15.0 | 15.0 | 15.0 | 15.0 | 15.0 | 15.0 | 15.0 | 15.0 | 15.0 |
| Vaseline | 15.0 | 15.0 | 15.0 | 15.0 | 15.0 | 15.0 | 15.0 | 15.0 | 15.0 |
| Beeswax | 3.0 | 3.0 | 3.0 | 3.0 | 3.0 | 3.0 | 3.0 | 3.0 | 3.0 |
| Sorbitan stearate | 3.0 | 3.0 | 3.0 | 3.0 | 3.0 | 3.0 | 3.0 | 3.0 | 3.0 |
| Polyoxyethylene cetyl ether | 2.0 | 2.0 | 2.0 | 2.0 | 2.0 | 2.0 | 2.0 | 2.0 | 2.0 |
| Glycerol | 5.0 | 5.0 | 5.0 | 5.0 | 5.0 | 5.0 | 5.0 | 5.0 | 5.0 |
| Dimethicone | 1.0 | 1.0 | 1.0 | 1.0 | 1.0 | 1.0 | 1.0 | 1.0 | 1.0 |
| Triethanolamine | Proper amount | Proper amount | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount | Proper amount | Proper amount |
| (a1) | 1.0 | 1.0 | 1.0 | 1.0 | — | — | — | — | 1.0 |
| (b1) | 0.5 | — | — | — | 0.5 | — | — | — | — |
| (b3) | — | 1.0 | — | — | — | 1.0 | — | — | — |
| (b7) | — | — | 0.2 | — | — | — | 0.2 | — | — |
| (b8) | — | — | — | 0.5 | — | — | — | 0.5 | — |
| Water | Remainder | Remainder | Remainder | Remainder | Remainder | Remainder | Remainder | Remainder | Remainder |
| Total | 100 | 100 | 100 | 100 | 100 | 100 | 100 | 100 | 100 |

TABLE 11

| Hair wax | Example | | | | |
|---|---|---|---|---|---|
| Composition | 71 | 72 | 73 | 74 | 75 |
| Vaseline | 5.0 | 5.0 | 5.0 | 5.0 | 5.0 |
| Glycerol monostearate | 10.0 | 10.0 | 10.0 | 10.0 | 10.0 |
| Polyoxyethylene hardened castor oil | 5.0 | 5.0 | 5.0 | 5.0 | 5.0 |
| Polyoxyethylene cetyl ether | 2.0 | 2.0 | 2.0 | 2.0 | 2.0 |
| Liquid paraffin | 8.0 | 8.0 | 8.0 | 8.0 | 8.0 |
| Stearic acid | 3.0 | 3.0 | 3.0 | 3.0 | 3.0 |
| Dimethicone | 5.0 | 5.0 | 5.0 | 5.0 | 5.0 |
| Triethanolamine | Proper amount | Proper amount | Proper amount | Proper amount | Proper amount |
| Glycerol | 3.0 | 3.0 | 3.0 | 3.0 | 3.0 |
| Antiseptic | Proper amount | Proper amount | Proper amount | Proper amount | Proper amount |
| Water | Remainder | Remainder | Remainder | Remainder | Remainder |
| (a1) | 3.0 | 3.0 | 3.0 | 3.0 | 3.0 |
| (b1) | 0.5 | — | — | — | — |
| (b3) | — | 1.0 | — | — | — |
| (b7) | — | — | 0.3 | — | — |
| (b8) | — | — | — | 0.5 | — |
| (b16) | — | — | — | — | 1.0 |
| Total | 100 | 100 | 100 | 100 | 100 |

TABLE 12

| Hair wax | Comparative Example | | | | | |
|---|---|---|---|---|---|---|
| Composition | 71 | 72 | 73 | 74 | 75 | 76 |
| Vaseline | 5.0 | 5.0 | 5.0 | 5.0 | 5.0 | 5.0 |
| Glycerol monostearate | 10.0 | 10.0 | 10.0 | 10.0 | 10.0 | 10.0 |
| Polyoxyethylene hardened castor oil | 5.0 | 5.0 | 5.0 | 5.0 | 5.0 | 5.0 |
| Polyoxyethylene cetyl ether | 2.0 | 2.0 | 2.0 | 2.0 | 2.0 | 2.0 |
| Liquid paraffin | 8.0 | 8.0 | 8.0 | 8.0 | 8.0 | 8.0 |
| Stearic acid | 3.0 | 3.0 | 3.0 | 3.0 | 3.0 | 3.0 |
| Dimethicone | 5.0 | 5.0 | 5.0 | 5.0 | 5.0 | 5.0 |
| Triethanolamine | Proper amount | Proper amount | Proper amount | Proper amount | Proper amount | Proper amount |
| Glycerol | 3.0 | 3.0 | 3.0 | 3.0 | 3.0 | 3.0 |
| Antiseptic | Proper amount | Proper amount | Proper amount | Proper amount | Proper amount | Proper amount |
| Water | Remainder | Remainder | Remainder | Remainder | Remainder | Remainder |
| (a1) | — | — | — | — | — | 3.0 |
| (b1) | 0.5 | — | — | — | — | — |
| (b3) | — | 1.0 | — | — | — | — |
| (b7) | — | — | 0.3 | — | — | — |
| (b8) | — | — | — | 0.5 | — | — |
| (b16) | — | — | — | — | 1.0 | — |
| Total | 100 | 100 | 100 | 100 | 100 | 100 |

As for the hair colorants, the components from 25% ammonia water to an oxidation dye and water (i.e., the components other than the components from 50% hydrogen peroxide to (b8)) listed in Table 13 were mixed at the ratios shown in Table 13, and the mixture was stirred at 80° C. until it became homogeneous, followed by cooling it to room temperature, preparing a first agent. Next, the components from 50% hydrogen peroxide to (b8) were mixed at the ratios shown in Table 13, and the mixture was stirred until it became homogeneous, preparing a second agent and thereby producing a hair colorant.

TABLE 13

| Hair colorant | Example | | | Comparative Example | | | |
|---|---|---|---|---|---|---|---|
| Composition | 81 | 82 | 83 | 81 | 82 | 83 | 84 |
| 25% ammonia water | 4.0 | 4.0 | 4.0 | 4.0 | 4.0 | 4.0 | 4.0 |
| Monoethanolamine | 1.0 | 1.0 | 1.0 | 1.0 | 1.0 | 1.0 | 1.0 |

TABLE 13-continued

| Hair colorant | Example | | | Comparative Example | | | |
|---|---|---|---|---|---|---|---|
| Composition | 81 | 82 | 83 | 81 | 82 | 83 | 84 |
| Propylene glycol | 1.5 | 1.5 | 1.5 | 1.5 | 1.5 | 1.5 | 1.5 |
| Isopropanol | 1.5 | 1.5 | 1.5 | 1.5 | 1.5 | 1.5 | 1.5 |
| Ammonium lauryl sulfate | 1.0 | 1.0 | 1.0 | 1.0 | 1.0 | 1.0 | 1.0 |
| Sodium sulfite | 0.1 | 0.1 | 0.1 | 0.1 | 0.1 | 0.1 | 0.1 |
| Oxidation dye | Proper amount | Proper amount | Proper amount | Proper amount | Proper amount | Proper amount | Proper amount |
| Water | 30.0 | 30.0 | 30.0 | 30.0 | 30.0 | 30.0 | 30.0 |
| 50% hydrogen peroxide | 6.0 | 6.0 | 6.0 | 6.0 | 6.0 | 6.0 | 6.0 |
| Phosphoric acid | 0.1 | 0.1 | 0.1 | 0.1 | 0.1 | 0.1 | 0.1 |
| Water | Remainder | Remainder | Remainder | Remainder | Remainder | Remainder | Remainder |
| (a1) | 1.0 | 1.0 | 1.0 | — | — | — | 1.0 |
| (b1) | 1.0 | — | — | 1.0 | — | — | — |
| (b2) | — | 1.0 | — | — | 1.0 | — | — |
| (b8) | — | — | 1.0 | — | — | 1.0 | — |
| Total | 100 | 100 | 100 | 100 | 100 | 100 | 100 |

In addition, the following water-soluble resins were used for the hair cosmetics:

(b12) polyquaternium-11 (Gafquat 755 N (trade name) manufactured by ISP corp.), which is a cationic synthetic polyvinyl polymer;

(b13) acrylic resin alkanolamine (PLASCIZE L-6330 (trade name) manufactured by Goo Chemical CO., LTD.), which is an anionic non-association type poly(meth)acrylate polymer;

(b14) (octylacrylamide/hydroxypropyl acrylate/butylaminoethyl methacrylate) copolymer (AMPHOMER 28-4910 (trade name) manufactured by National Starch and Chemical Company), which is an amphoteric non-association type synthetic poly(meth)acrylate polymer;

(b15) (vinylpyrrolidone/VA) copolymer (Luviskol VA 64 (trade name) manufactured by BASF Corporation), which is a nonionic synthetic polyvinyl polymer; and (b16) polyethylene glycol (polyethylene glycol 6,000 (trade name) manufactured by Wako Pure Chemical Industries, Ltd.), which is a synthetic polyether polymer.

As examples of the make-up cosmetics, mascaras, eyeliners, manicures, liquid eye shadows and liquid foundations were produced.

As for the mascaras, the components from stearic acid to liquid paraffin listed in Table 14 were mixed at the ratios shown in Table 14, and the mixture was dissolved at 80° C., preparing an oil phase. Next, the components from propylene glycol to water were mixed at the ratios shown in Table 14, and the mixture was dissolved at 80° C., followed by dispersing a pigment in the mixture to prepare a water phase. The oil phase was charged into the water phase, and the mixture was emulsified with a homomixer. Then, an acrylic resin emulsion was gradually added to the mixture at the ratio shown in Table 14, and the whole was stirred with a homomixer. Thereafter, the mixture was cooled to room temperature, thereby producing a mascara.

TABLE 14

| Mascara | Example | | | Comparative Example | | | |
|---|---|---|---|---|---|---|---|
| Composition | 91 | 92 | 93 | 91 | 92 | 93 | 94 |
| Stearic acid | 5.0 | 5.0 | 5.0 | 5.0 | 5.0 | 5.0 | 5.0 |
| Beeswax | 6.0 | 6.0 | 6.0 | 6.0 | 6.0 | 6.0 | 6.0 |
| Liquid paraffin | 3.0 | 3.0 | 3.0 | 3.0 | 3.0 | 3.0 | 3.0 |
| Propylene glycol | 5.0 | 5.0 | 5.0 | 5.0 | 5.0 | 5.0 | 5.0 |
| Bentonite | 2.0 | 2.0 | 2.0 | 2.0 | 2.0 | 2.0 | 2.0 |
| Sodium lauryl sulfate | 0.5 | 0.5 | 0.5 | 0.5 | 0.5 | 0.5 | 0.5 |
| (a1) | 3.0 | 3.0 | 3.0 | — | — | — | 3.0 |
| (b1) | 1.0 | — | — | 1.0 | — | — | — |
| (b2) | — | 1.0 | — | — | 1.0 | — | — |
| (b8) | — | — | 1.0 | — | — | 1.0 | — |
| Triethanolamine | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount |
| Water | Remainder | Remainder | Remainder | Remainder | Remainder | Remainder | Remainder |
| Pigment | 10.0 | 10.0 | 10.0 | 10.0 | 10.0 | 10.0 | 10.0 |
| Acrylic resin emulsion (resin content 45%) | 30.0 | 30.0 | 30.0 | 30.0 | 30.0 | 30.0 | 30.0 |
| Total | 100 | 100 | 100 | 100 | 100 | 100 | 100 |

As for the eyeliners, the components from polyoxyethylene sorbitan monostearate to (b8) listed in Table 15 were mixed at the ratios shown in Table 15, and the mixture was uniformly dispersed with a colloid mill. To this dispersion, the components from glycerol to an acrylic resin emulsion were successively mixed at the ratios shown in Table 15, and the whole was stirred until it became homogeneous, thereby producing an eyeliner.

As for the liquid eye shadows, the components from microcrystalline wax to sorbitan monostearate listed in Table 17 were mixed at the ratios shown in Table 17, and the mixture was dissolved at 80° C., preparing an oil phase. Next, the components from (a1) to water were mixed at the ratios shown in Table 17, and the mixture was dissolved at 80° C., followed by dispersing a pigment in the mixture to prepare a water phase. The oil phase was charged into the water phase,

TABLE 15

| Eyeliner | Example | | | Comparative Example | | | |
|---|---|---|---|---|---|---|---|
| Composition | 95 | 96 | 97 | 95 | 96 | 97 | 98 |
| Polyoxyethylene sorbitan monostearate | 1.0 | 1.0 | 1.0 | 1.0 | 1.0 | 1.0 | 1.0 |
| Titanium dioxide | 2.0 | 2.0 | 2.0 | 2.0 | 2.0 | 2.0 | 2.0 |
| Iron oxide | 5.0 | 5.0 | 5.0 | 5.0 | 5.0 | 5.0 | 5.0 |
| Triethanolamine | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount |
| Water | Remainder | Remainder | Remainder | Remainder | Remainder | Remainder | Remainder |
| (a1) | 3.0 | 3.0 | 3.0 | — | — | — | 3.0 |
| (b1) | 1.0 | — | — | 1.0 | — | — | — |
| (b2) | — | 1.0 | — | — | 1.0 | — | — |
| (b8) | — | — | 1.0 | — | — | 1.0 | — |
| Glycerol | 5.0 | 5.0 | 5.0 | 5.0 | 5.0 | 5.0 | 5.0 |
| Acetyl tributyl citrate | 1.0 | 1.0 | 1.0 | 1.0 | 1.0 | 1.0 | 1.0 |
| Acrylic resin emulsion (resin content 45%) | 50.0 | 50.0 | 50.0 | 50.0 | 50.0 | 50.0 | 50.0 |
| Total | 100 | 100 | 100 | 100 | 100 | 100 | 100 |

As for the manicures, the components from polyoxyethylene sorbitan monostearate to water listed in Table 16 were mixed at the ratios shown in Table 16, and the mixture was stirred until it became homogeneous. To this mixture, a pigment was added and dispersed at the ratio shown in Table 16, and the components from (a1) to an acrylic resin emulsion were successively added at the ratio shown in Table 16, followed by stirring until it became homogeneous, thereby producing a manicure.

TABLE 16

| Manicure | Example | | | Comparative Example | | | |
|---|---|---|---|---|---|---|---|
| Composition | 101 | 102 | 103 | 101 | 102 | 103 | 104 |
| Polyoxyethylene sorbitan monostearate | 1.0 | 1.0 | 1.0 | 1.0 | 1.0 | 1.0 | 1.0 |
| Carbitol | 5.0 | 5.0 | 5.0 | 5.0 | 5.0 | 5.0 | 5.0 |
| Diethyl phthalate | 4.0 | 4.0 | 4.0 | 4.0 | 4.0 | 4.0 | 4.0 |
| Triethanolamine | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount |
| Water | Remainder | Remainder | Remainder | Remainder | Remainder | Remainder | Remainder |
| Pigment | 2.0 | 2.0 | 2.0 | 2.0 | 2.0 | 2.0 | 2.0 |
| (a1) | 3.0 | 3.0 | 3.0 | — | — | — | 3.0 |
| (b1) | 1.0 | — | — | 1.0 | — | — | — |
| (b2) | — | 1.0 | — | — | 1.0 | — | — |
| (b8) | — | — | 1.0 | — | — | 1.0 | — |
| Acrylic resin emulsion (resin content 45%) | 60.0 | 60.0 | 60.0 | 60.0 | 60.0 | 60.0 | 60.0 |
| Total | 100 | 100 | 100 | 100 | 100 | 100 | 100 | and the mixture was emulsified with a homomixer. Then, an acrylic resin emulsion was gradually added to the mixture at the ratio shown in Table 17, and the whole was stirred with a homomixer. Thereafter, the mixture was cooled to room temperature, thereby producing a liquid eye shadow.

TABLE 17

| Liquid eye shadow | Example | | | Comparative Example | | | |
|---|---|---|---|---|---|---|---|
| Composition | 106 | 107 | 108 | 106 | 107 | 108 | 109 |
| Microcrystalline wax | 3.0 | 3.0 | 3.0 | 3.0 | 3.0 | 3.0 | 3.0 |
| Stearic acid | 3.0 | 3.0 | 3.0 | 3.0 | 3.0 | 3.0 | 3.0 |
| Liquid paraffin | 10.0 | 10.0 | 10.0 | 10.0 | 10.0 | 10.0 | 10.0 |
| Lanolin | 1.0 | 1.0 | 1.0 | 1.0 | 1.0 | 1.0 | 1.0 |
| Sorbitan monostearate | 2.0 | 2.0 | 2.0 | 2.0 | 2.0 | 2.0 | 2.0 |
| (a1) | 3.0 | 3.0 | 3.0 | — | — | — | 3.0 |
| (b1) | 1.0 | — | — | 1.0 | — | — | — |
| (b3) | — | 1.0 | — | — | 1.0 | — | — |
| (b8) | — | — | 1.0 | — | — | 1.0 | — |
| Glycerol | 4.0 | 4.0 | 4.0 | 4.0 | 4.0 | 4.0 | 4.0 |
| Triethanolamine | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount |
| Water | Remainder | Remainder | Remainder | Remainder | Remainder | Remainder | Remainder |
| Acrylic resin emulsion (resin content 45%) | 25.0 | 25.0 | 25.0 | 25.0 | 25.0 | 25.0 | 25.0 |
| Total | 100 | 100 | 100 | 100 | 100 | 100 | 100 |

As for the liquid foundations, the components from (a1) to water listed in Table 18 were mixed at the ratios shown in Table 18, and the mixture was dispersed at 70° C. with a homomixer until it became homogeneous. Next, the components from talc to iron oxide were sufficiently mixed at the ratios shown in Table 18, and the mixture was added to the above-described dispersion. The whole was dispersed at 70° C. with a homomixer to prepare a water phase. The components from stearic acid to liquid paraffin were mixed at the ratios shown in Table 18, and the mixture was dissolved at 80° C., preparing an oil phase. This oil phase was charged into the above-described water phase, and the mixture was emulsified at 70° C. with a homomixer. Thereafter, the mixture was cooled to room temperature, thereby producing a liquid foundation.

TABLE 18

| Liquid foundation | Example | | | Comparative Example | | | |
|---|---|---|---|---|---|---|---|
| Composition | 111 | 112 | 113 | 111 | 112 | 113 | 114 |
| (a1) | 3.0 | 3.0 | 3.0 | — | — | — | 3.0 |
| (b1) | 1.0 | — | — | 1.0 | — | — | — |
| (b3) | — | 1.0 | — | — | 1.0 | — | — |
| (b8) | — | — | 1.0 | — | — | 1.0 | — |
| Bentonite | 0.5 | 0.5 | 0.5 | 0.5 | 0.5 | 0.5 | 0.5 |
| Polyoxyethylene monostearate | 1.0 | 1.0 | 1.0 | 1.0 | 1.0 | 1.0 | 1.0 |
| Propylene glycol | 10.0 | 10.0 | 10.0 | 10.0 | 10.0 | 10.0 | 10.0 |
| Triethanolamine | Proper amount | Proper amount | Proper amount | Proper amount | Proper amount | Proper amount | Proper amount |
| Antiseptic | Proper amount | Proper amount | Proper amount | Proper amount | Proper amount | Proper amount | Proper amount |
| Water | Remainder | Remainder | Remainder | Remainder | Remainder | Remainder | Remainder |
| Talc | 3.0 | 3.0 | 3.0 | 3.0 | 3.0 | 3.0 | 3.0 |
| Titanium dioxide | 5.0 | 5.0 | 5.0 | 5.0 | 5.0 | 5.0 | 5.0 |
| Red oxide | 0.5 | 0.5 | 0.5 | 0.5 | 0.5 | 0.5 | 0.5 |
| Iron oxide | 1.0 | 1.0 | 1.0 | 1.0 | 1.0 | 1.0 | 1.0 |
| Stearic acid | 2.5 | 2.5 | 2.5 | 2.5 | 2.5 | 2.5 | 2.5 |
| Isohexadecyl alcohol | 7.0 | 7.0 | 7.0 | 7.0 | 7.0 | 7.0 | 7.0 |
| Glycerol monostearate | 2.0 | 2.0 | 2.0 | 2.0 | 2.0 | 2.0 | 2.0 |
| Liquid lanolin | 2.0 | 2.0 | 2.0 | 2.0 | 2.0 | 2.0 | 2.0 |
| Liquid paraffin | 8.0 | 8.0 | 8.0 | 8.0 | 8.0 | 8.0 | 8.0 |
| Total | 100 | 100 | 100 | 100 | 100 | 100 | 100 |

As examples of the skin care cosmetics, O/W skin creams, W/O skin creams, sunscreens, milky lotions and packs were produced.

As for the O/W skin creams, the components from propylene glycol to water (i.e., the components other than the components from C12-15 alkyl benzoate to an antiseptic) listed in Table 19 were mixed at the ratios shown in Table 19, and the mixture was dissolved at 80° C., preparing a water phase. Next, the components from C12-15 alkyl benzoate to an antiseptic were mixed at the ratios shown in Table 19, and the mixture was dissolved at 80° C., preparing an oil phase. The oil phase was charged into the water phase, and the mixture was emulsified with a homomixer, followed by stirring until it became homogeneous. Thereafter, the mixture was cooled to room temperature, thereby producing an O/W skin cream.

TABLE 19

| O/W skin cream | Example | | | | Comparative Example | | | | |
|---|---|---|---|---|---|---|---|---|---|
| Composition | 121 | 122 | 123 | 124 | 121 | 122 | 123 | 124 | 125 |
| Propylene glycol | 3.0 | 3.0 | 3.0 | 3.0 | 3.0 | 3.0 | 3.0 | 3.0 | 3.0 |
| Triethanolamine | 0.5 | 0.5 | 0.5 | 0.5 | 0.5 | 0.5 | 0.5 | 0.5 | 0.5 |
| (a1) | 3.0 | 3.0 | 3.0 | 3.0 | — | — | — | — | 3.0 |
| (b1) | 1.0 | — | — | — | 1.0 | — | — | — | — |
| (b3) | — | 1.0 | — | — | — | 1.0 | — | — | — |
| (b8) | — | — | 1.0 | — | — | — | 1.0 | — | — |
| (b17) | — | — | — | 1.0 | — | — | — | 1.0 | — |
| Water | Remainder | Remainder | Remainder | Remainder | Remainder | Remainder | Remainder | Remainder | Remainder |
| C12-15 alkyl benzoate | 5.0 | 5.0 | 5.0 | 5.0 | 5.0 | 5.0 | 5.0 | 5.0 | 5.0 |
| Octyl palmitate | 5.0 | 5.0 | 5.0 | 5.0 | 5.0 | 5.0 | 5.0 | 5.0 | 5.0 |
| Cetyl alcohol | 1.0 | 1.0 | 1.0 | 1.0 | 1.0 | 1.0 | 1.0 | 1.0 | 1.0 |
| Stearic acid | 2.0 | 2.0 | 2.0 | 2.0 | 2.0 | 2.0 | 2.0 | 2.0 | 2.0 |
| Dimethicone polyol | 1.0 | 1.0 | 1.0 | 1.0 | 1.0 | 1.0 | 1.0 | 1.0 | 1.0 |
| Antiseptic | Proper amount | Proper amount | Proper amount | Proper amount | Proper amount | Proper amount | Proper amount | Proper amount | Proper amount |
| Total | 100 | 100 | 100 | 100 | 100 | 100 | 100 | 100 | 100 |

As for the W/O skin creams, the components from propylene glycol to water (i.e., the components other than the components from microcrystalline wax to an antiseptic) listed in Table 20 were mixed at the ratios shown in Table 20, and the mixture was dissolved at 70° C., preparing a water phase. Next, the components from microcrystalline wax to an antiseptic were mixed at the ratios shown in Table 20, and the mixture was dissolved at 70° C., preparing an oil phase. The oil phase was charged into the water phase, and the mixture was emulsified with a homomixer, followed by stirring until it became homogeneous. Thereafter, the mixture was cooled to room temperature, thereby producing a W/O skin cream.

TABLE 20

| W/O skin cream | Example | | | | Comparative Example | | | | |
|---|---|---|---|---|---|---|---|---|---|
| Composition | 131 | 132 | 133 | 134 | 131 | 132 | 133 | 134 | 135 |
| Propylene glycol | 5.0 | 5.0 | 5.0 | 5.0 | 5.0 | 5.0 | 5.0 | 5.0 | 5.0 |
| (a1) | 5.0 | 5.0 | 5.0 | 5.0 | — | — | — | — | 5.0 |
| (b1) | 0.5 | — | — | — | 0.5 | — | — | — | — |
| (b3) | — | 1.0 | — | — | — | 1.0 | — | — | — |
| (b8) | — | — | 1.0 | — | — | — | 1.0 | — | — |
| (b17) | — | — | — | 1.0 | — | — | — | 1.0 | — |
| Water | Remainder | Remainder | Remainder | Remainder | Remainder | Remainder | Remainder | Remainder | Remainder |
| Microcrystalline wax | 9.0 | 9.0 | 9.0 | 9.0 | 9.0 | 9.0 | 9.0 | 9.0 | 9.0 |
| Solid paraffin | 2.0 | 2.0 | 2.0 | 2.0 | 2.0 | 2.0 | 2.0 | 2.0 | 2.0 |
| Beeswax | 9.0 | 9.0 | 9.0 | 9.0 | 9.0 | 9.0 | 9.0 | 9.0 | 9.0 |
| Vaseline | 5.0 | 5.0 | 5.0 | 5.0 | 5.0 | 5.0 | 5.0 | 5.0 | 5.0 |
| Reduced lanolin | 5.0 | 5.0 | 5.0 | 5.0 | 5.0 | 5.0 | 5.0 | 5.0 | 5.0 |
| Squalane | 34.0 | 34.0 | 34.0 | 34.0 | 34.0 | 34.0 | 34.0 | 34.0 | 34.0 |
| Hexadecyl adipate | 10.0 | 10.0 | 10.0 | 10.0 | 10.0 | 10.0 | 10.0 | 10.0 | 10.0 |
| Glycerol monooleate | 3.5 | 3.5 | 3.5 | 3.5 | 3.5 | 3.5 | 3.5 | 3.5 | 3.5 |
| POE(25) sorbitan monooleate | 1.0 | 1.0 | 1.0 | 1.0 | 1.0 | 1.0 | 1.0 | 1.0 | 1.0 |

TABLE 20-continued

| W/O skin cream | Example | | | | Comparative Example | | | | |
|---|---|---|---|---|---|---|---|---|---|
| Composition | 131 | 132 | 133 | 134 | 131 | 132 | 133 | 134 | 135 |
| Antiseptic | Proper amount | Proper amount | Proper amount | Proper amount | Proper amount | Proper amount | Proper amount | Proper amount | Proper amount |
| Total | 100 | 100 | 100 | 100 | 100 | 100 | 100 | 100 | 100 |

As for the sunscreens, the components from sorbeth-30 to water (i.e., the components other than the components from ethanol to dimethicone) listed in Table 21 were mixed at the ratios shown in Table 21 and the mixture was dissolved at 80° C., preparing a water phase. Next, the components from ethanol to dimethicone were mixed at the ratios shown in Table 21, and the mixture was dissolved at 80° C., preparing an oil phase. The oil phase was charged into the water phase, and the mixture was emulsified with a homomixer, followed by stirring until it became homogeneous. Thereafter, the mixture was cooled to room temperature, thereby producing a sunscreen.

TABLE 21

| Sunscreen | Example | | | | Comparative Example | | | | |
|---|---|---|---|---|---|---|---|---|---|
| Composition | 141 | 142 | 143 | 144 | 141 | 142 | 143 | 144 | 145 |
| Sorbeth-30 | 3.0 | 3.0 | 3.0 | 3.0 | 3.0 | 3.0 | 3.0 | 3.0 | 3.0 |
| (a1) | 5.0 | 5.0 | 5.0 | 5.0 | — | — | — | — | 5.0 |
| (b1) | 0.5 | — | — | — | 0.5 | — | — | — | — |
| (b3) | — | 1.0 | — | — | — | 1.0 | — | — | — |
| (b8) | — | — | 1.0 | — | — | — | 1.0 | — | — |
| (b17) | — | — | — | 1.0 | — | — | — | 1.0 | — |
| Antiseptic | Proper amount | Proper amount | Proper amount | Proper amount | Proper amount | Proper amount | Proper amount | Proper amount | Proper amount |
| Water | Remainder | Remainder | Remainder | Remainder | Remainder | Remainder | Remainder | Remainder | Remainder |
| Ethanol | 3.0 | 3.0 | 3.0 | 3.0 | 3.0 | 3.0 | 3.0 | 3.0 | 3.0 |
| Isostearyl alcohol | 6.0 | 6.0 | 6.0 | 6.0 | 6.0 | 6.0 | 6.0 | 6.0 | 6.0 |
| Octyl methoxy cinnamate | 5.0 | 5.0 | 5.0 | 5.0 | 5.0 | 5.0 | 5.0 | 5.0 | 5.0 |
| Octyl salicylate | 5.0 | 5.0 | 5.0 | 5.0 | 5.0 | 5.0 | 5.0 | 5.0 | 5.0 |
| C12-15 alkyl benzoate | 4.0 | 4.0 | 4.0 | 4.0 | 4.0 | 4.0 | 4.0 | 4.0 | 4.0 |
| Sorbitan monooleate | 2.0 | 2.0 | 2.0 | 2.0 | 2.0 | 2.0 | 2.0 | 2.0 | 2.0 |
| Polysorbate 20 | 1.0 | 1.0 | 1.0 | 1.0 | 1.0 | 1.0 | 1.0 | 1.0 | 1.0 |
| Dimethicone | 1.0 | 1.0 | 1.0 | 1.0 | 1.0 | 1.0 | 1.0 | 1.0 | 1.0 |
| Total | 100 | 100 | 100 | 100 | 100 | 100 | 100 | 100 | 100 |

As for the milky lotions, the components from dipropylene glycol to water (i.e., the components other than the components from stearic acid to sorbitan monooleate) listed in Table 22 were mixed at the ratios shown in Table 22, and the mixture was dissolved at 70° C., preparing a water phase. Next, the components from stearic acid to sorbitan monooleate were mixed at the ratios shown in Table 22, and the mixture was dissolved at 70° C., preparing an oil phase. The oil phase was charged into the water phase, and the mixture was emulsified with a homomixer, followed by stirring until it became homogeneous. Thereafter, the mixture was cooled to room temperature, thereby producing a milky lotion.

TABLE 22

| Milky lotion | Example | | | | Comparative Example | | | | |
|---|---|---|---|---|---|---|---|---|---|
| Composition | 151 | 152 | 153 | 154 | 151 | 152 | 153 | 154 | 155 |
| Dipropylene glycol | 5.0 | 5.0 | 5.0 | 5.0 | 5.0 | 5.0 | 5.0 | 5.0 | 5.0 |
| Triethanolamine | Proper amount | Proper amount | Proper amount | Proper amount | Proper amount | Proper amount | Proper amount | Proper amount | Proper amount |
| (a1) | 3.0 | 3.0 | 3.0 | 3.0 | — | — | — | — | 3.0 |
| (b1) | 0.5 | — | — | — | 0.5 | — | — | — | — |
| (b3) | — | 1.0 | — | — | — | 1.0 | — | — | — |
| (b8) | — | — | 1.0 | — | — | — | 1.0 | — | — |
| (b17) | — | — | — | 1.0 | — | — | — | 1.0 | — |
| Antiseptic | Proper amount | Proper amount | Proper amount | Proper amount | Proper amount | Proper amount | Proper amount | Proper amount | Proper amount |
| Water | Remainder | Remainder | Remainder | Remainder | Remainder | Remainder | Remainder | Remainder | Remainder |
| Stearic acid | 2.0 | 2.0 | 2.0 | 2.0 | 2.0 | 2.0 | 2.0 | 2.0 | 2.0 |
| Cetyl alcohol | 1.5 | 1.5 | 1.5 | 1.5 | 1.5 | 1.5 | 1.5 | 1.5 | 1.5 |
| Vaseline | 4.0 | 4.0 | 4.0 | 4.0 | 4.0 | 4.0 | 4.0 | 4.0 | 4.0 |
| Squalane | 5.0 | 5.0 | 5.0 | 5.0 | 5.0 | 5.0 | 5.0 | 5.0 | 5.0 |
| Glyceryl tri-2-ethylhexanoate | 2.0 | 2.0 | 2.0 | 2.0 | 2.0 | 2.0 | 2.0 | 2.0 | 2.0 |
| Sorbitan monooleate | 2.0 | 2.0 | 2.0 | 2.0 | 2.0 | 2.0 | 2.0 | 2.0 | 2.0 |
| Total | 100 | 100 | 100 | 100 | 100 | 100 | 100 | 100 | 100 |

As for the packs, the components from titanium oxide to water (i.e., the components other than the components from ethanol to an antiseptic) listed in Table 23 were mixed at the ratios shown in Table 23, and the mixture was dissolved at 80° C., preparing a water phase. Next, the components from ethanol to an antiseptic were mixed at the ratios shown in Table 23, and the mixture was dissolved at 70° C., preparing an oil phase. The oil phase was charged into the water phase, and the mixture was emulsified with a homomixer, followed by stirring until it became homogeneous. Thereafter, the mixture was cooled to room temperature, thereby producing a pack.

TABLE 23

| Pack | Example | | | | Comparative Example | | | | |
|---|---|---|---|---|---|---|---|---|---|
| Composition | 161 | 162 | 163 | 164 | 161 | 162 | 163 | 164 | 165 |
| Titanium oxide | 5.0 | 5.0 | 5.0 | 5.0 | 5.0 | 5.0 | 5.0 | 5.0 | 5.0 |
| Talc | 10.0 | 10.0 | 10.0 | 10.0 | 10.0 | 10.0 | 10.0 | 10.0 | 10.0 |
| Sorbitol | 5.0 | 5.0 | 5.0 | 5.0 | 5.0 | 5.0 | 5.0 | 5.0 | 5.0 |
| Polyvinyl acetate emulsion (pure content 45%) | 25.0 | 25.0 | 25.0 | 25.0 | 25.0 | 25.0 | 25.0 | 25.0 | 25.0 |
| (a1) | 5.0 | 5.0 | 5.0 | 5.0 | — | — | — | — | 5.0 |
| (b1) | 3.0 | — | — | — | 3.0 | — | — | — | — |
| (b3) | — | 3.0 | — | — | — | 3.0 | — | — | — |
| (b8) | — | — | 2.0 | — | — | — | 2.0 | — | — |
| (b18) | — | — | — | 5.0 | — | — | — | 5.0 | — |
| Water | Remainder | Remainder | Remainder | Remainder | Remainder | Remainder | Remainder | Remainder | Remainder |
| Ethanol | 8.0 | 8.0 | 8.0 | 8.0 | 8.0 | 8.0 | 8.0 | 8.0 | 8.0 |
| POE sorbitan monostearate | 1.0 | 1.0 | 1.0 | 1.0 | 1.0 | 1.0 | 1.0 | 1.0 | 1.0 |
| Jojoba oil | 2.0 | 2.0 | 2.0 | 2.0 | 2.0 | 2.0 | 2.0 | 2.0 | 2.0 |
| Squalane | 2.0 | 2.0 | 2.0 | 2.0 | 2.0 | 2.0 | 2.0 | 2.0 | 2.0 |
| Antiseptic | Proper amount | Proper amount | Proper amount | Proper amount | Proper amount | Proper amount | Proper amount | Proper amount | Proper amount |
| Total | 100 | 100 | 100 | 100 | 100 | 100 | 100 | 100 | 100 |

In addition, the following water-soluble resins were also used for the skin care cosmetics:

(b17) polyacrylamide (SEPIGEL 501 (trade name) manufactured by Seiwa Kasei Co., Ltd.), which is a nonionic synthetic polyvinyl polymer; and (b18) polyvinyl alcohol (Kuraray Poval (trade name) manufactured by Kuraray Co., Ltd.), which is a nonionic synthetic polyvinyl polymer.

The above-described aqueous composition of the present invention includes: (A) at least one selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18 and a cross-linked product of an acyl modified starch with a carbon number of 2 to 18; and (B) a water-soluble polymer material. Therefore, they can alleviate at least one of the problems of insufficient temporal stability, insufficient viscosity increase, being incapable of being used in a variety of pH ranges and being incapable of providing sufficient thixotropy.

The aqueous composition of the present invention can more effectively address the problems that the viscosity increase is insufficient, that sufficient thixotropy cannot be provided and that the temporal stability is insufficient, when the water-soluble polymer material (B) includes a poly(meth)acrylate polymer. In addition, it can address the problem of being incapable of being used in a variety of pH ranges, by selecting the type (ionicity) of the poly(meth)acrylate polymer. Furthermore, it can further address the problems of insufficient viscosity increase and insufficient temporal stability, when the poly(meth)acrylate polymer is an association type polymer.

The aqueous composition of the present invention can more effectively address the problems of insufficient viscosity increase, being incapable of providing sufficient thixotropy and insufficient temporal stability, when the water-soluble polymer material (B) includes a nonionic cellulose polymer.

In addition, it can more effectively address the problems of insufficient viscosity increase and insufficient temporal stability, when the water-soluble polymer material (B) includes a cationic cellulose polymer.

Furthermore, the aqueous composition of the present invention can more effectively address the problems of insufficient viscosity increase, being incapable of providing sufficient thixotropy and insufficient temporal stability, when the water-soluble polymer material (B) includes a poly(meth) acrylic acid polymer.

In addition, it can more effectively address the problems of insufficient viscosity increase, being incapable of providing sufficient thixotropy and insufficient temporal stability, when the water-soluble polymer material (B) includes xanthan gum.

The aqueous composition of the present invention can more effectively address the problems of insufficient viscosity increase, being incapable of providing sufficient thixotropy and insufficient temporal stability, when the weight ratio of (A)/(B) is 30/1 to 0.5/1.

Additionally, it can more effectively address the problems of insufficient viscosity increase, being incapable of providing sufficient thixotropy and insufficient temporal stability, when (A) constitutes 0.5 to 5.5 wt % of the whole of a cosmetic obtained by mixing the aqueous composition.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. Method of preparing a cosmetic composition comprising:

adding 0.5 to 5.5 weight % of at least one starch chosen from a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18, and a cross-linked product of an acyl modified starch with a carbon number of 2 to 18, to an aqueous composition, based on total weight of the aqueous composition, adding a water-soluble polymer material to the aqueous composition such that the weight ratio of the at least one starch to the water-soluble polymer in the aqueous composition is from 0.5:1 to 30:1, and mixing the aqueous composition with a cosmetic composition to form a cosmetic.

2. Method according to claim 1 wherein the water-soluble polymer material is chosen from poly(meth)acrylate polymer, nonionic cellulose polymer, cationic cellulose polymer, poly(meth)acrylic acid polymer, xanthan gum.

3. Method according to claim 2 wherein the water-soluble polymer material is at least poly(meth)acrylate polymer and the poly(meth)acrylate polymer is at least an association type polymer.

4. Method according to claim 2 wherein the water-soluble polymer material is at least nonionic cellulose polymer and the nonionic cellulose polymer is at least hydroxyalkyl cellulose.

5. Method according to claim 2 wherein the water-soluble polymer material is at least cationic cellulose polymer and the cationic cellulose polymer is at least O-[2-hydroxy-3-(trimethylammonio)propyl]hydroxyethyl cellulose chloride.

6. Method according to claim 2 wherein the water-soluble polymer material is at least xanthan gum that has been heat-treated at 60° C. or higher.

7. Method according to claim 1 wherein the at least one starch is at least one starch cross-linked by phosphorylation.

8. Method according to claim 7 wherein the at least one cross-linked starch is cross-linked by alkanedicarboxylic acid or alkenedicarboxylic acid.

9. Method according to claim 1 wherein the at least one starches has an amylopectin content of at least 70 wt %.

10. Method according to claim 1 wherein the cosmetic is a cleansing cosmetic, hair cosmetic, make-up cosmetic or skin care cosmetic.

11. Method according to claim 10 wherein the cosmetic is a cleansing cosmetic and the cleansing cosmetic is at least one chosen from shampoo, rinse, conditioner, hand soap, body soap, facial wash and make-up cleanser.

12. Method according to claim 10 wherein the cosmetic is a hair cosmetic and the hair cosmetic is chosen from hair foam, hair gel, nonaerosol pump spray, hair cream, hair wax, acidic hair dye, hair colorant, perming agent and bleaching agent.

13. Method according to claim 10 wherein the cosmetic is a make-up cosmetic and the make-up cosmetic is chosen from manicure, mascara, eyeliner, eye shadow, liquid foundation, lipstick and cheek rouge.

14. Method according to claim 10 wherein the cosmetic is a skin care cosmetic and the skin care cosmetic is chosen from foundation, pack, sunscreen, skin lotion, milky lotion and skin cream.

* * * * *

UNITED STATES PATENT AND TRADEMARK OFFICE
CERTIFICATE OF CORRECTION

PATENT NO. : 8,362,089 B2  Page 1 of 1
APPLICATION NO. : 12/021077
DATED : January 29, 2013
INVENTOR(S) : Hashimoto It is certified that error appears in the above-identified patent and that said Letters Patent is hereby corrected as shown below:

In the Specification

Column 6, line 12, "nice" -- should read -- rice --.

Column 12, line 7, "hydroxyethylimidazoliinum" -- should read -- hydroxyethylimidazolinium --.

Column 19, Table 2, Column 10, "Proper" -- should read -- Proper amount --.

Signed and Sealed this
Fifth Day of August, 2014

Michelle K. Lee
*Deputy Director of the United States Patent and Trademark Office*